(12) United States Patent
Haacke

(10) Patent No.: US 10,451,697 B2
(45) Date of Patent: Oct. 22, 2019

(54) SYSTEMS AND METHODS FOR STRATEGICALLY ACQUIRED GRADIENT ECHO IMAGING

(71) Applicant: SPINTECH, INC., Bingham Farms, MI (US)

(72) Inventor: E. Mark Haacke, Detroit, MI (US)

(73) Assignee: SPINTECH, INC., Bingham Farms, MI (US)

( * ) Notice: Subject to any disclaimer, the term of this patent is extended or adjusted under 35 U.S.C. 154(b) by 93 days.

(21) Appl. No.: 15/659,353

(22) Filed: Jul. 25, 2017

(65) Prior Publication Data

US 2019/0033418 A1    Jan. 31, 2019

(51) Int. Cl.

| | |
|---|---|
| *G01V 3/00* | (2006.01) |
| *G01R 33/561* | (2006.01) |
| *G01R 33/567* | (2006.01) |
| *A61B 5/055* | (2006.01) |
| *G01R 33/50* | (2006.01) |
| *G01R 33/565* | (2006.01) |

(Continued)

(52) U.S. Cl.
CPC .......... *G01R 33/5613* (2013.01); *A61B 5/055* (2013.01); *G01R 33/4818* (2013.01); *G01R 33/50* (2013.01); *G01R 33/5615* (2013.01); *G01R 33/5676* (2013.01); *G01R 33/56554* (2013.01); *A61B 5/7203* (2013.01); *A61B 5/7264* (2013.01); *A61B 2576/026* (2013.01); *G01R 33/246* (2013.01)

(58) Field of Classification Search
CPC .............. G01R 33/543; G01R 33/5659; G01R 33/3415; G01R 33/36; A61B 5/055

USPC .......................................................... 324/309
See application file for complete search history.

(56) References Cited

U.S. PATENT DOCUMENTS

| | | |
|---|---|---|
| 6,603,989 B1 | 8/2003 | Yablonskiy |
| 8,502,538 B2 | 8/2013 | Dannels et al. |

(Continued)

OTHER PUBLICATIONS

International Search Report and Written Opinion, PCT/US2017/043991, Magnetic Resonance Creative Imaging Inc., 13 pages (dated Oct. 5, 2017).

*Primary Examiner* — Walter L Lindsay, Jr.
*Assistant Examiner* — Frederick Wenderoth
(74) *Attorney, Agent, or Firm* — Foley & Lardner, LLP

(57) ABSTRACT

Variable flip angle techniques with constraints for reconstructing MR images include a processor generating a $T_{1app}$ map representing a spatial distribution of $T_{1app}$ within an anatomical region using a first MR dataset corresponding to a first flip angle (FA) and a second MR dataset corresponding to a second FA. The processor can estimate a first and second transmit RF field maps by scaling the $T_{1app}$ map by a first constant value of $T_1$ associated with a first tissue type and a second constant value of $T_1$ associated with a second tissue type, respectively. The processor can generate a third transmit RF field map using the first and second transmit RF field maps, and use the third transmit RF field map to construct MR images of the anatomical region. Weighted subtraction images can be created with improved contrast-to-noise ratio compared to images of the first and second MR datasets.

20 Claims, 13 Drawing Sheets

(51) Int. Cl.
*G01R 33/48* (2006.01)
*A61B 5/00* (2006.01)
*G01R 33/24* (2006.01)

(56) References Cited

U.S. PATENT DOCUMENTS

| | | | |
|---|---|---|---|
| 9,625,547 B2 | 4/2017 | Heule et al. | |
| 2002/0173713 A1* | 11/2002 | Pfefferbaum | A61B 5/055 600/407 |
| 2010/0004527 A1* | 1/2010 | Dale | G01R 33/56341 600/410 |
| 2011/0025327 A1 | 2/2011 | Deoni et al. | |
| 2011/0026799 A1 | 2/2011 | Nehrke et al. | |
| 2011/0218405 A1* | 9/2011 | Avinash | A61B 5/00 600/300 |
| 2011/0280458 A1* | 11/2011 | Flohr | G06T 5/50 382/131 |
| 2013/0187648 A1* | 7/2013 | Freed | G01N 24/081 324/303 |
| 2013/0207653 A1 | 8/2013 | Ito et al. | |
| 2015/0073258 A1* | 3/2015 | Mazer | G01R 33/50 600/410 |
| 2016/0291107 A1* | 10/2016 | Rosen | G01R 33/543 |
| 2017/0086720 A1 | 3/2017 | Schabel et al. | |
| 2017/0103531 A1* | 4/2017 | Markov | G06T 7/11 |

\* cited by examiner

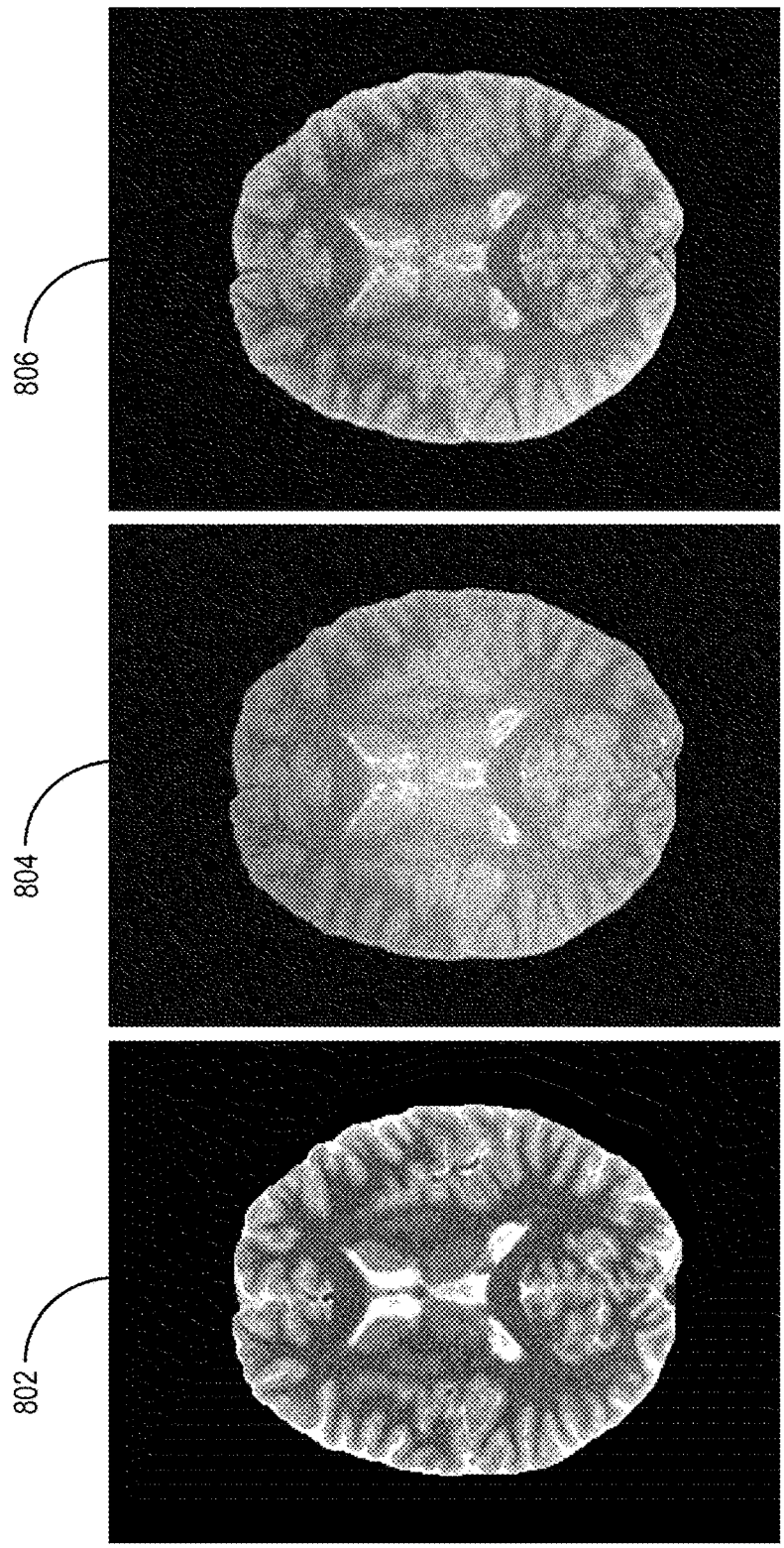

SYSTEMS AND METHODS FOR STRATEGICALLY ACQUIRED GRADIENT ECHO IMAGING

BACKGROUND OF THE DISCLOSURE

The present disclosure relates generally to the field of magnetic resonance imaging (MRI). In particular, this disclosure relates to methods and systems for quantitative magnetic resonance imaging (qMRI) using variable flip angle (VFA) techniques.

Magnetic resonance imaging (MRI) is an imaging modality that uses magnetic fields to reconstruct a structure of scanned objects of interest. An MRI scanner includes a magnet for generating a strong static magnetic field, such as a magnetic field in the range of 0.10 Tesla (T) to 7 T, and radio frequency (RF) transceivers for transmitting and/or receiving RF signals. When a body is placed in the generated static magnetic field, the Hydrogen protons within the body align to the magnetic field. An RF pulse is applied in the presence of an oscillating B1 field to tip the spins so that there is a bulk magnetization remaining in the transverse field. When the RF pulse is turned off, the Hydrogen protons return to alignment with the static magnetic field, the longitudinal component increasing and the transverse component decreasing. At a chosen time point, referred to as the sampling time, or echo time, or gradient echo time, data is collected and the received signal is used to reconstruct an image of the scanned body or a part thereof. In the current disclosure, various VFA techniques for reconstructing MR images based on collected MR datasets are described.

SUMMARY OF THE DISCLOSURE

According to at least one aspect, a magnetic resonance imaging (MRI) system can include a MRI scanner, at least one processor, and a memory, with computer code instructions stored thereon. The MRI scanner can be configured to acquire a first magnetic resonance (MR) dataset corresponding to a first flip angle and a second MR dataset corresponding to a second flip angle by imaging an anatomical region using at least one echo time. The computer code instructions, when executed by the at least one processor, cause the at least one processor to generate an apparent longitudinal relaxation time ($T_{1app}$) map, representing a spatial distribution of T1app within the anatomical region using the first MR dataset and the second MR dataset. The at least one processor can estimate a first transmit RF field map by scaling the $T_{1app}$ map by a first constant value of longitudinal relaxation time ($T_1$). The first constant value of $T_1$ can be associated with a first tissue type within the anatomical region. The at least one processor can estimate a second transmit RF field map by scaling the $T_{1app}$ map by a second constant value of $T_1$. The second constant value of $T_1$ can be associated with a second tissue type within the anatomical region. The processor can generate a third transmit RF field map using the estimated first transmit RF field map and the estimated second transmit RF field map. The third transmit RF field map can represent a spatial distribution of the transmit RF field within the anatomical region.

The anatomical region can be a human brain where the first tissue type can be white matter, and the second tissue type can be gray matter. The at least one processor can estimate a fourth transmit RF field map by scaling the $T_{1app}$ map by a third constant value of $T_1$. The third constant value of $T_1$ can be associated with a third tissue type within the anatomical region. Generating the third transmit RF field map can include using the estimated first transmit RF field map, the estimated second transmit RF field map, and the estimated fourth transmit RF field map. The anatomical region can be a human brain where the first tissue type can be white matter, the second tissue type can be gray matter, and the third tissue type can be cerebro-spinal fluid. The at least one processor can generate a first longitudinal relaxation time ($T_1$) map by dividing the $T_{1app}$ map by the square of the third transmit RF field map. The first $T_1$ map can represent the spatial distribution of $T_1$ within the anatomical region.

The at least one processor can generate an apparent spin density ($SD_{app}$) map using the first MR dataset and the second MR dataset. The $SD_{app}$ map can represent a spatial distribution of $SD_{app}$ within the anatomical region. The at least one processor can generate a first spin density (SD) map by scaling the $SD_{app}$ map by the third transmit RF field map. The at least one processor can synthesize, using the third transmit RF field map, the first $T_1$ map, and the first SD map, a third MR dataset corresponding to a third flip angle such that at least a first sub-region of the anatomical region corresponding to the first tissue type and a second sub-region of the anatomical region corresponding to the second tissue type are isointense. The at least one processor can estimate a receive RF field map using the synthesized third MR dataset. The receive RF field map can represent a spatial distribution of a receive RF field within the anatomical region. The at least one processor can generate a second SD map by scaling the first SD map by the estimated receive RF field map.

The at least one processor can scale the first MR dataset by the receive RF field map, scale the second MR data set by the receive MR dataset, and generate an image representing a weighted subtraction of the scaled first MR dataset from the scaled second MR dataset. The at least one processor can generate an image representing a weighted subtraction of the first MR dataset from the second MR dataset.

The at least one processor can estimate a plurality of transmit RF field maps for a plurality of subjects, and generate a transmit RF field template using an averaging of the estimated plurality of transmit RF field maps for the plurality of subjects. The at least one processor can generate a second $T_1$ map using the $T_{1app}$ map and the transmit RF field template. The at least one processor can generate a spin density (SD) map using an estimated $SD_{app}$ map, the transmit RF field template, and an estimated receive RF field map.

According to at least one aspect, a method for magnetic resonance imaging (MRI) can include at least one processor receiving a first magnetic resonance (MR) dataset corresponding to a first flip angle and a second MR dataset corresponding to a second flip angle. The first MR dataset and the second MR dataset can be acquired by imaging an anatomical region using at least one echo time. The method can include the at least one processor generating an apparent longitudinal relaxation time ($T_{1app}$) map, representing a spatial distribution of $T_{1app}$ within the anatomical region using the first MR dataset and the second MR dataset within the anatomical region. The method can include the at least one processor estimating a first transmit RF field map by scaling the $T_{1app}$ map by a first constant value of longitudinal relaxation time ($T_1$). The first constant value of $T_1$ can be associated with a first tissue type within the anatomical region. The method can include the at least one processor estimating a second transmit RF field map by scaling the $T_{1app}$ map by a second constant value of $T_1$. The second constant value of $T_1$ can be associated with a second tissue type within the anatomical region. The method can include the at least one processor generating a third transmit RF field map using the estimated first transmit RF field map and the estimated second transmit RF field map. The third transmit RF field map can represent a spatial distribution of the transmit RF field within the anatomical region.

The method can further include the at least one processor estimating a fourth transmit RF field map by scaling the $T_{1app}$ map by a third constant value of $T_1$. The third constant value of $T_1$ can be associated with a third tissue type within the anatomical region. Generating the third transmit RF field map can include using the estimated first transmit RF field map, the estimated second transmit RF field map, and the estimated fourth transmit RF field map. The anatomical region can be a human brain where the first tissue type can be white matter, the second tissue type can be gray matter, and the third tissue type can be cerebro-spinal fluid. The method can further include the at least one processor generating a first longitudinal relaxation time ($T_1$) map by dividing the $T_{1app}$ map by the square of the third transmit RF field map. The first $T_1$ map can represent the spatial distribution of $T_1$ within the anatomical region.

The method can further include the at least one processor generating an apparent spin density ($SD_{app}$) map using the first MR dataset and the second MR dataset. The $SD_{app}$ map can represent a spatial distribution of $SD_{app}$ within the anatomical region. The at least one processor can generate a first spin density (SD) map by scaling the $SD_{app}$ map by the third transmit RF field map. The at least one processor can synthesize, using the third transmit RF field map, the first $T_1$ map, and the first SD map, a third MR dataset corresponding to a third flip angle such that at least a first sub-region of the anatomical region corresponding to the first tissue type and a second sub-region of the anatomical region corresponding to the second tissue type are isointense. The at least one processor can estimate a receive RF field map using the synthesized third MR dataset. The receive RF field map can represent a spatial distribution of a receive RF field within the anatomical region. The at least one processor can generate a second SD map by scaling the first SD map by the estimated receive RF field map.

The method can further include the at least one processor scaling the first MR dataset by the receive RF field map, scaling the second MR data set by the receive MR dataset, and generating an image representing a weighted subtraction of the scaled first MR dataset from the scaled second MR dataset. The method can further include the at least one processor generating an image representing a weighted subtraction of the first MR dataset from the second MR dataset.

The method can further include the at least one processor estimating a plurality of transmit RF field maps for a plurality of subjects, and generating a transmit RF field template using an averaging of the estimated plurality of transmit RF field maps for the plurality of subjects. The method can further include the at least one processor generating a second $T_1$ map using the $T_{1app}$ map and the transmit RF field template. The method can further include the at least one processor generating a spin density (SD) map using an estimated $SD_{app}$ map, the transmit RF field template, and an estimated receive RF field map.

According to at least one aspect, a computer-readable medium includes computer code instructions stored thereon. The computer code instructions when executed by at least one processor cause a method for magnetic resonance imaging (MRI) to be performed. The method can include the at least one processor receiving a first magnetic resonance (MR) dataset corresponding to a first flip angle and a second MR dataset corresponding to a second flip angle. The first MR dataset and the second MR dataset can be acquired by imaging an anatomical region using at least one echo time. The method can include the at least one processor generating an apparent longitudinal relaxation time ($T_{1app}$) map, representing a spatial distribution of $T_{1app}$ within the anatomical region using the first MR dataset, the second MR dataset and a constant value for a transmit radio frequency (RF) field within the anatomical region. The method can include the at least one processor estimating a first transmit RF field map by scaling the $T_{1app}$ map by a first constant value of longitudinal relaxation time ($T_1$). The first constant value of $T_1$ can be associated with a first tissue type within the anatomical region. The method can include the at least one processor estimating a second transmit RF field map by scaling the $T_{1app}$ map by a second constant value of $T_1$. The second constant value of $T_1$ can be associated with a second tissue type within the anatomical region. The method can include the at least one processor generating a third transmit RF field map using the estimated first transmit RF field map and the estimated second transmit RF field map. The third transmit RF field map can represent a spatial distribution of the transmit RF field within the anatomical region.

BRIEF DESCRIPTION OF THE DRAWINGS

FIGS. 8A-8C show images illustrating examples of an estimate of a $T_1$ map, an estimate of an apparent spin density ($SD_{app}$) map, and an estimate of a spin density (SD) map, respectively;

DETAILED DESCRIPTION

Figure 1:
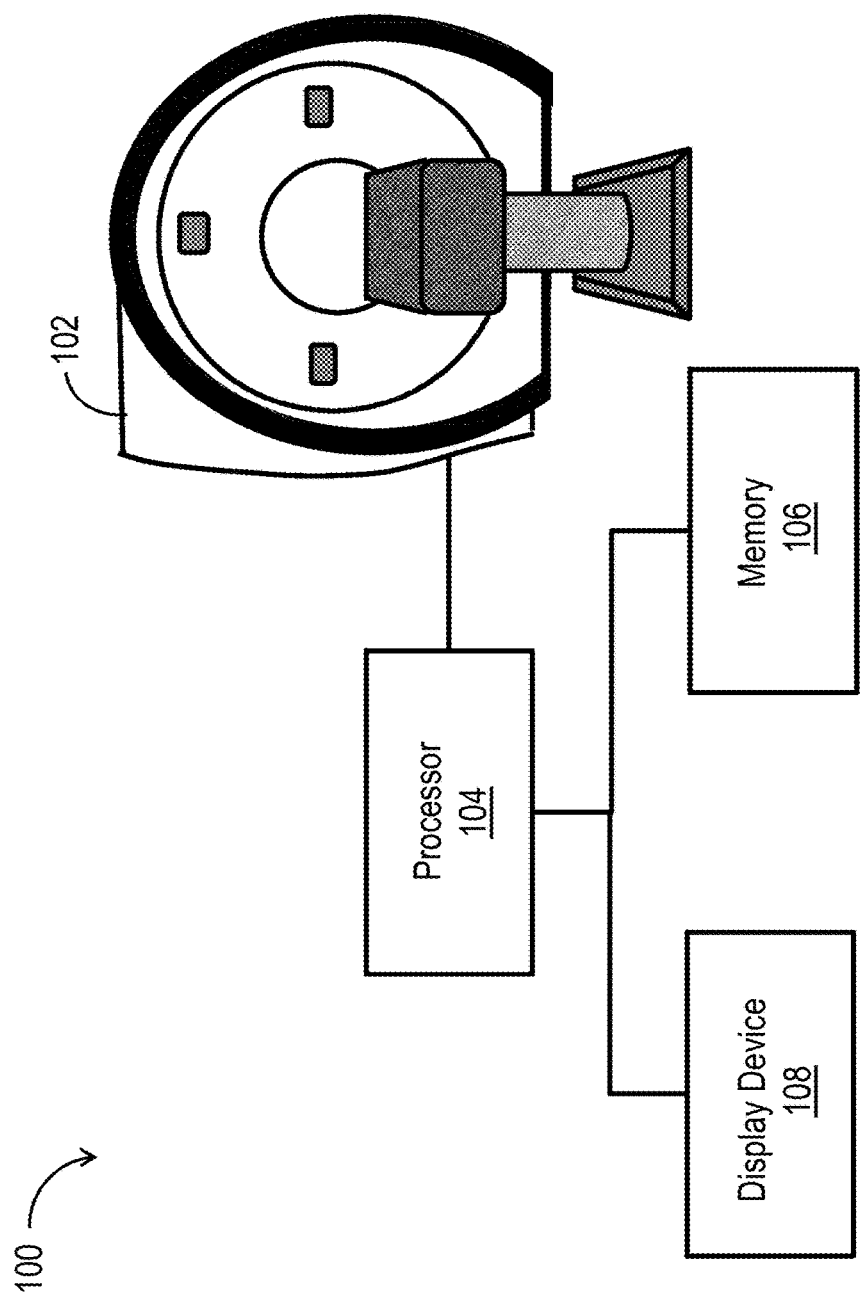
FIG. 1 is a block diagram illustrating a magnetic resonance imaging (MRI) system, according to inventive concepts of this disclosure.

Quantitative magnetic resonance imaging (qMRI) involves measuring and/or using signal intensities or relative signal intensities to distinguish between different types of tissues or to identify abnormal tissues. By quantifying the tissue properties, it becomes easier to develop methods to both segment and classify normal and abnormal tissue types. The use of quantitative spin density (SD), longitudinal relaxation time ($T_1$), transverse magnetization decay rate ($T_2^*$), and quantitative susceptibility mapping (QSM) has important clinical applications today. For example, quantitative $T_1$ imaging has potential utility in studying atherosclerosis in cardiovascular imaging, tumors, stroke, and multiple sclerosis. Also, quantitative SD mapping plays a significant role and has been used to study edema and changes in tissue water content after treatment. Generally, this type of tissue quantification makes it possible to follow the response of the tissue to treatment in a more rigorous fashion.

Quantitative $T_1$ imaging and quantitative SD mapping can be achieved using variable flip angle (VFA) techniques. Using VFA methods involves acquisition of MR data for a plurality of different flip angles. In particular, a MRI scanner can acquire multiple spoiled gradient echo datasets with different nominal flip angles, and use the acquired datasets to appropriately quantify $T_1$ and/or SD. While VFA techniques are characterized by the ease of MR data collection, VFA-based techniques call for accurate knowledge of the radiofrequency (RF) excitation (or transmit) field ($B_{1t}$) or flip angles (FA) as a function of position. In fact, the ability to accurately calculate the $T_1$ map based on VFA datasets depends on accurate knowledge of the spatial distribution of the transmit RF field ($B_{1t}$) map. Also, reconstruction of the SD map involves the use of the receive RF field ($B_{1r}$) map. In some implementations, a MRI scanner or a respective processor can compute the transmit RF field $B_{1t}$ by using acquired datasets for at least three different flip angles (FAs) including a dataset associated with a relatively large FA, for example, compared to the other two FAs. Using datasets corresponding to less than three FAs or relatively small FAs can render the problem of constructing the transmit RF field $B_{1t}$ ill-posed and can call for additional constraints to remedy the ill-posedness of the problem. Examples of such constraints to address the ill-posedness can include using a single tissue such as fat to determine the $B_{1t}$ field distribution for breast imaging, or using constraints on the relationship between $T_1$ and SD for white matter and gray matter.

In the current disclosure, methods and systems for strategically acquired gradient echo (STAGE) imaging with improved image quality and quantitative data are described. STAGE imaging can allow for comprehensive rapid imaging using acquired datasets corresponding to two FAs. Also, the systems and methods for STAGE imaging described herein allow for reliable and accurate reconstruction of T1 and SD maps.

FIG. 1 is a block diagram illustrating a magnetic resonance imaging (MRI) system 100, according to inventive concepts of this disclosure. In brief overview, the MRI system 100 can include a MRI scanner 102, a processor 104, a memory 106, and a display device 108. The processor 104 can be communicatively coupled to the MRI scanner 102, the memory 106 and the display device 108.

The MRI scanner 102 can include a magnet (not shown in FIG. 1) for generating a strong static magnetic field, such as a magnetic field in the range of 0.1 Tesla (T) to 7 T, and a plurality of radio frequency (RF) coils (not shown in FIG. 1) for transmitting and/or receiving RF signals. The RF coils can include transmit RF coils and receive RF coils. The RF transmit coils can emit RF pulses to excite a subject, such as an anatomical region of a patient, according to a MRI pulse sequence. The receive RF coils can record MRI signals generated by the subject following the emission of the RF pulses. The RF coils may include RF transceivers capable of alternately transmitting and receiving RF signals. The RF coils can acquire MRI data according to an RF spoiled gradient data acquisition. The recorded MRI signals can be associated with two different FAs.

The imaging system 100 can include one or more processors 104. The one or more processors 104 can include a processor integrated within the MRI scanner 102, a processor of a computing device communicatively coupled to the MRI scanner 102, or a combination thereof. The memory 106 can include a memory component of the MRI scanner 102, a memory component of a computing device communicatively coupled to the MRI scanner 102, or a combination thereof. The memory 106 can include computer executable instructions, which when executed by the one or more processors 104, can cause the one or more processors 104 to perform methods for STAGE imaging described herein. The memory 106 can store MRI data acquired by the MRI scanner 102, and the processor(s) 104 can access such data from the memory 106. The memory 106 can receive and store images generated by the processor(s) 104 based on the MRI data acquired by the scanner 102.

The display device 108 can include a cathode ray tube (CRT) display, a light emitting diode (LED) display, an organic light emitting diode (OLED) display, a plasma display panel (PDP), a liquid crystal display (LCD), or other display known to a person of ordinary skill in the art. The display device 108 may be a stand-alone device or a display of a computing device (e.g., a desktop, laptop, or tablet) communicatively coupled to the MRI scanner 102. The display device 108 can include a touch screen. The display device 108 can receive image data from the processor 104 or the memory 106 and display the received image data. For example, upon reconstructing MRI images based on data acquired by the MRI scanner 102, the processor 104 can provide the reconstructed images for display on the display device 108.

The signal intensity for an RF spoiled gradient echo data acquisition as a function of flip angle θ can be described as:

$$S = SD \cdot B_{1r} \cdot e^{-TE/T2^*} \cdot \sin(B_{1t} \cdot \theta) \cdot \frac{(1-E1)}{(1-E1\cos(B_{1t} \cdot \theta))} \quad (1)$$

where T1 is the longitudinal relation time, SD is the spin density, TR is the repetition time, TE is the echo time, $B_{1t}$ is the transmit RF field, $B_{1r}$ is the receive RF field (also referred to as RF coil sensitivity or bias field), and E1=exp(−TR/$T_1$). Here we have assumed that the B1t term is normalized to unity when the correct flip angle is obtained. Multiplying both sides of equation (1) by $$\frac{(1-E1\cos(B_{1t} \cdot \theta))}{\sin(B_{1t} \cdot \theta)},$$

equation (1) can be rewritten as:

$$\frac{S(\theta)}{\sin(B_{1t}\theta)} = E1 \cdot \frac{S(\theta)}{\tan(B_{1t}\theta)} + SD_{eff} \cdot (1-E1), \quad (2)$$

where $SD_{eff} = SD \cdot B_{1r} \cdot e^{-TE/T2^*}$ represents the effective spin density.

According to equation (2), $$\frac{S(\theta)}{\sin(B_{1t}\theta)}$$

can be viewed as a linear function of $$\frac{S(\theta)}{\tan(B_{1t}\theta)}.$$

Specifically, for data collected for different nominal excitation flip angles, one can fit the transformed data to a line with slope $E_1$ and ordinate intercept (or x-axis crossing) at $SD_{eff} \cdot (1-E_1)$. As such, one can determine the value of $E_1$ by computing the slope of a line defined by at least two data points corresponding to at least two FAs in the $$\left( \frac{S(\theta)}{\tan(B_{1t}\theta)}, \frac{S(\theta)}{\sin(B_{1t}\theta)} \right)$$

coordinate system. Also, using the determined $E_1$ value and the point of intersection between the x-axis and line formed by the at least two data points one can determine the value of $SD_{eff}$. However, due to inhomogeneities of the $B_{1t}$ field, the measured flip angle may be different from the actual flip angle value chosen to run the scan and this can lead to significant error in the estimation of $T_1$, especially at high magnetic fields. Therefore, an accurate estimation of $T_1$ calls for an accurate knowledge of the transmit RF field $B_{1t}$.

For low FAs and where TR<<T1, equation (1) can be approximated as:

$$S(\theta) = SD_{eff} \cdot B_{1t}\theta \bigg/ \left(1 + \frac{(B_{1t}\theta)^2}{\theta_E^2}\right), \quad (3)$$

where the angle $\theta_E$ is defined as $\cos \theta_E = \exp(-TR/T_1)$. Using equation (3), the apparent spin density ($SD_{app}$) and the apparent longitudinal relaxation time ($T_{1app}$) can be derived as:

$$SD_{app} = B_{1t} \cdot SD_{eff} \quad (4)$$

$$T_{1app} = T_1 \cdot B_{1t}^2 \quad (5)$$

Considering equations (3)-(5), the apparent spin density $SD_{app}$ is linearly proportional to $B_{1t}$, and the apparent longitudinal relaxation time $T_{1app}$ is linearly proportional to $B_{1t}^2$. Thus a 10% error in $B_{1t}$ (or a 10% in FA if the actual FA is $\theta'=B_{1t}\theta$), can result in a 20% error in $T_1$ estimation and a 10% error in SD estimation. Hence, accurate reconstruction of $T_1$ and/or SD maps calls for accurate estimation of the $B_{1t}$ map.

Figure 2:
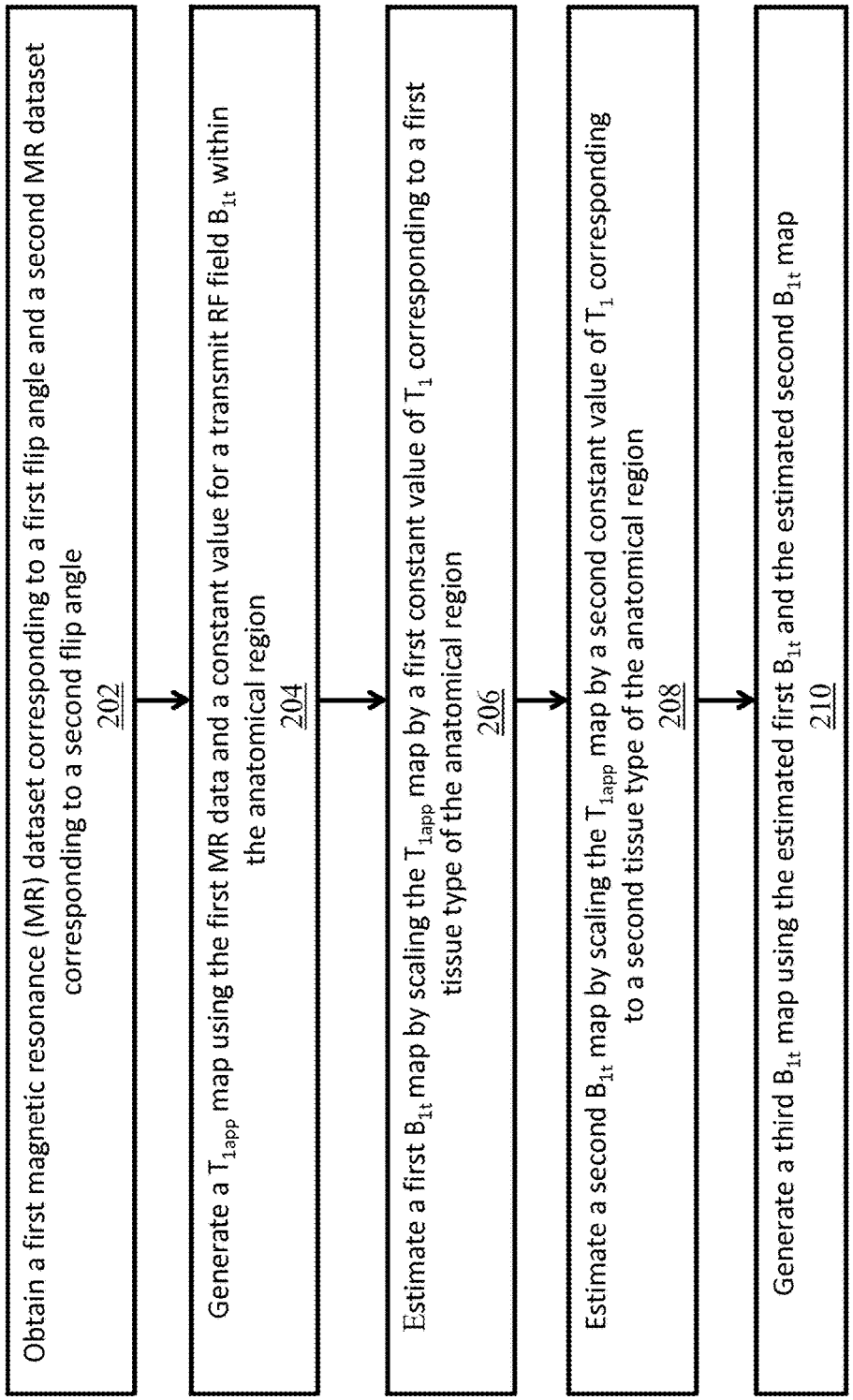
FIG. 2 is a flowchart illustrating a method 200 for magnetic resonance imaging (MRI), according to inventive concepts of this disclosure.

FIG. 2 is a flowchart illustrating a method 200 for magnetic resonance imaging (MRI). In brief overview, the method 200 can include obtaining (or receiving) a first magnetic resonance (MR) dataset corresponding to a first flip angle and a second MR dataset corresponding to a second flip angle (step 202), and generating an apparent longitudinal relaxation time ($T_{1app}$) map using the first MR data, the second MR data and a constant value for a transmit radio frequency (RF) field within the anatomical region (step 204). The method 200 can also include estimating a first transmit RF field map by scaling the $T_{1app}$ map by a first constant value of longitudinal relaxation time ($T_1$) (step 206), estimating a second transmit RF field map by scaling the T1app map by a second constant value of $T_1$ (step 208), and generating a third transmit RF field map using the estimated first transmit RF field map and the estimated second transmit RF field map (step 210).

The method 200 can include obtaining (or receiving) a first magnetic resonance (MR) dataset corresponding to a first flip angle and a second MR dataset corresponding to a second flip angle (step 202). The scanner 102 can acquire the first MR dataset and the second MR dataset by imaging an anatomical region using at least one echo time TE. The processor 104 can provide a user interface (UI), e.g., on the display device 108, to allow a user to select settings for MR data acquisition. The processor 102 can cause the MR scanner 102 to image the anatomical region according to the selected settings. The selected settings can indicate MR data acquisitions using two separate FAs. The selected settings may be indicative of spoiled gradient echo MR data acquisition (e.g., using one or more spoiled gradient echo MR sequences). The anatomical region to be imaged can include a human brain or other organ or part of a patient's body.

The processor 104 can cause the MR scanner 102 (or the respective RF coils) to excite the anatomical region with RF pulses and record MR signals generated by the anatomical region according to the selected settings. In particular, the receive RF coils of the MR scanner 102 can record a first set of MR signals associated with a first FA and a second set of MR signals associated with a second FA. The relationship between the recorded MR signals and the corresponding FAs satisfies equation (1) and/or (2). Obtaining the first and second MR data sets can include the processor 104 receiving the recorded signals from the MR scanner 102 and generating a respective MR image for each MR dataset (or set of MR signals).

Figure 3B:
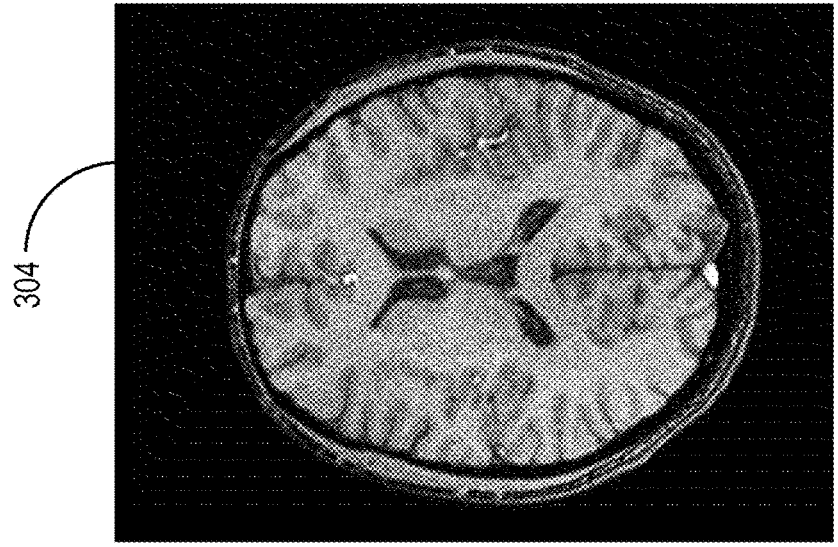
FIGS. 3A and 3B show two MR images of a brain corresponding to two different flip angles.
Figure 3A:
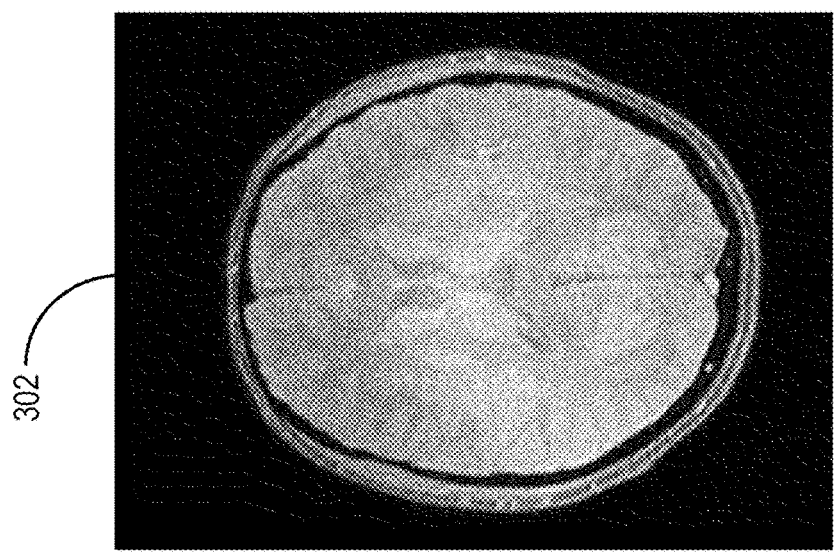

Referring to FIGS. 3A and 3B, two MR images of a brain corresponding to two different FAs are shown. For example, FIG. 3A shows an image 302 of MR data acquired using a FA equal to 6° and FIG. 3B shows an image 304 of MR data acquired using a FA equal to 24°. The repetition time TR used in acquiring the MR data illustrated in FIGS. 3A and 3B is equal to 25 milliseconds (ms). The values of the FAs associated with the images in FIGS. 3A and 3B are chosen for illustrative purposes and are not to be interpreted as limiting. For example, other angle values (other than 6° and/or 24°) can be used for MR data acquisition given that the low FA (among the two FAs) is less than the Ernst angle and the large FA is greater than the Ernst angle. The processor 104 can reconstruct the images shown in FIGS. 3A and 3B by taking the inverse Fourier transform of the recorded signals associated with the corresponding FAs, respectively.

Referring back to FIG. 2, the method 200 can include generating an apparent longitudinal relaxation time ($T_{1app}$) map using the first MR dataset, the second MR dataset, and a constant value for a transmit RF field $B_{1t}$ within the anatomical region (step 204). The $T_{1app}$ map represents a spatial distribution of $T_{1app}$ within the anatomical region. In general and considering equation (5), $T_{1app}$ can be spatially varying even within a region associated with a single tissue due to the spatial inhomogeneity of $B_{1t}$. For instance, $T_{1app}$ values can have a relatively large variance within a region representing one tissue. If there is a standard $B_{1t}$ available for all people, then that can be used to find local $T_1$ values from person to person. However, the lack of such standard value (or standard map) of $B_{1t}$ calls for methods or techniques to accurately estimate the $B_{1t}$ map. Generating the $T_{1app}$ map (step 204) can be viewed as determining a first estimate of the $T_{1app}$ map to be used to reconstruct the $B_{1t}$ map.

The processor 104 can calculate $T_{1app}$ on a pixel-by-pixel basis using equation (2) and assuming a normalized constant value for $B_{1t}$, e.g., equal to 1, within the anatomical region. Specifically, the processor 104 can first determine E1 for each pixel as the slope in equation (2) of a line defined based on the data points associated with the different FAs. Specifically, considering data points $S(\theta_1)$ and $S(\theta_2)$ corresponding to FAs $\theta_1$ and $\theta_2$, respectively, E1 can be computed as $$E1 = \left(\frac{S(\theta_1)}{\sin(B_{1t}\theta_1)} - \frac{S(\theta_2)}{\sin(B_{1t}\theta_2)}\right) / \left(\frac{S(\theta_1)}{\tan(B_{1t}\theta_1)} - \frac{S(\theta_2)}{\tan(B_{1t}\theta_2)}\right). \quad (6)$$

The processor 104 can determine an estimate of $T_1$ using the computed E1 and the repetition time TR since E1=exp(-TR/$T_1$). The processor 104 can then compute $T_{1app}$ for each pixel according to equation (5) using the estimated value of $T_1$ and the constant value of $B_{1t}$, and therefore generate the $T_{1app}$ map.

Figure 4B:
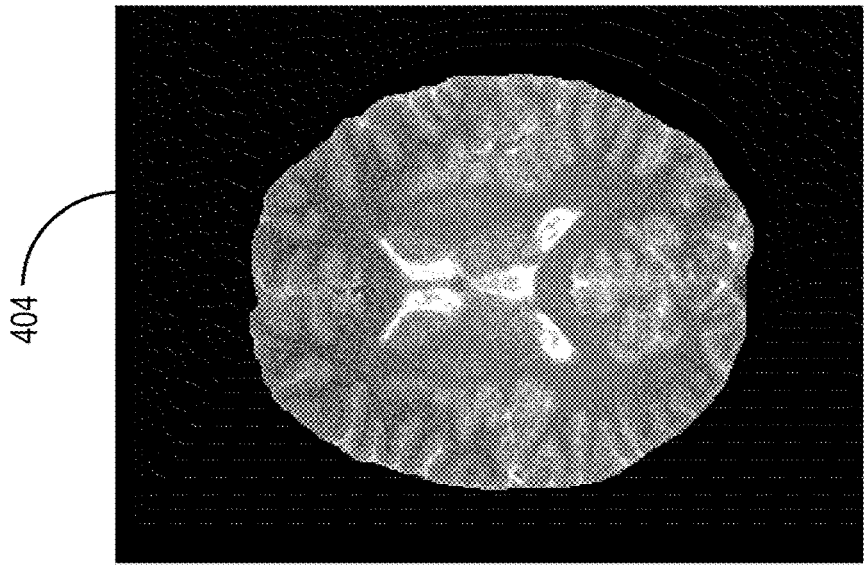
FIG. 4B shows an image of a first estimate of transmit RF field ($B_{1t}$) map generated using the $T_{1app}$ map shown in FIG. 4A.
Figure 4A:
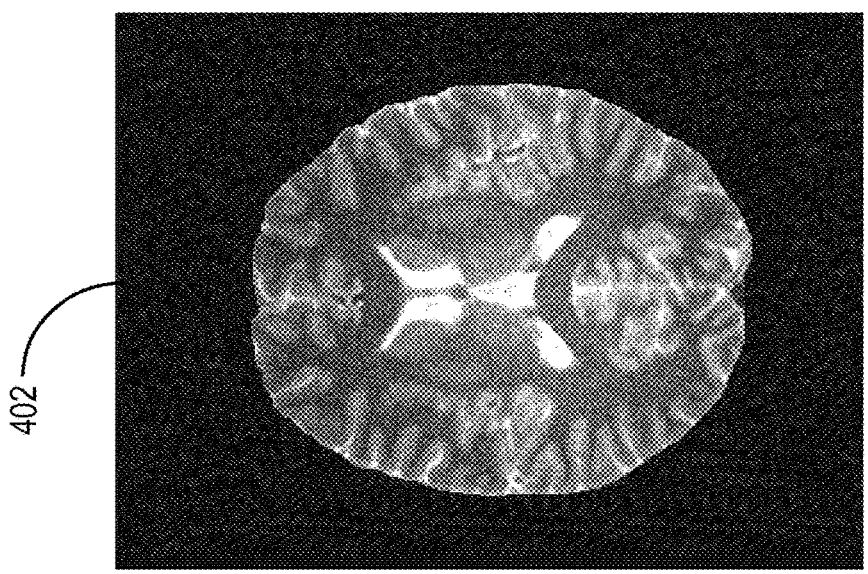
FIG. 4A shows an image depicting an example apparent longitudinal relaxation time ($T_{1app}$) map.

Referring to FIG. 4A, an image 402 of the $T_{1app}$ map is depicted. The $T_{1app}$ map shown in FIG. 4A is computed as described above on a pixel by pixel basis using the MR data shown in FIGS. 3A and 3B and a normalized constant value of $B_{1t}$ equal to 1. The MR data is acquired using a value of TR equal to 25 ms.

The method 200 can include the processor 104 estimating a first transmit RF field map by scaling the $T_{1app}$ map by a first constant value of $T_1$ (step 206), and estimating a second transmit RF field map by scaling the $T_{1app}$ map by a second constant value of $T_1$ (step 208). The first constant value of $T_1$ can correspond to a first tissue type within the anatomical region and the second constant value of $T_1$ can correspond to a second tissue type within the anatomical region. For example, the first tissue type can be white matter and the second tissue type can be gray matter. In general, there is no three-dimensional (3D) reliable and accurate standard for validating human brain $T_1$ measurements. Also, $T_1$ can be influenced by many factors, such as temperature, chemical exchange and perfusion. Values of $T_1$ values for both gray matter and white matter recorded by various researchers show substantial variations. However, despite such variations, the ratio of $T_1$ values for gray matter divided by $T_1$ values for white matter appears fairly stable across various measurements by different researchers. Specifically, the ratio is about 1.7. Accordingly, the first constant value of $T_1$ can be set to 1000 ms, whereas the second constant value of $T_1$ can be set to 1700 ms. In some implementations, other values of $T_1$ for the white matter and gray matter can be selected. For example, the $T_1$ value for the white matter can be set to any value in the range of 800 to 1200 ms, and the $T_1$ value for the gray matter can be set to be equal 1.7 times the $T_1$ value for the whit matter. Also, for other types of tissue (e.g., other than gray matter and/or white matter), different $T_1$ values can be used.

The processor 104 can generate the first estimate of the $B_{1t}$ map by scaling (or dividing) the $T_{1app}$ value at each pixel by the first constant value of $T_1$. Referring to FIG. 4B, an image 404 of the first estimate of the $B_{1t}$ map generated using the $T_{1app}$ map shown in FIG. 4A. The first estimate of the $B_{1t}$ map shown in FIG. 4B is computed using a constant value of $T_1$ equal to 1000 ms and corresponding to white matter. The processor 104 can generate the second estimate of the $B_{1t}$ map by scaling (or dividing) the $T_{1app}$ value at each pixel by the second constant value of $T_1$. The processor 104 can also generate masks for the first issue type and the second issue type within the anatomical region using at least one of the first estimate and the second estimate of the $B_{1t}$ map. For instance, the processor 104 can use the first estimate of the $B_{1t}$ map determined using a constant value of $T_1$ corresponding to white matter to generate a mask of white matter and a mask of gray matter. The estimates of the $B_{1t}$ map are characterized by low spatial frequency content and can be adequate for segmenting the anatomical region into various regions corresponding to different tissue types. The processor 104 can apply a high-pass filter to the first estimate of the $B_{1t}$ map to distinguish between white matter and gray matter regions. The processor 104 may apply a low-pass filter to the first estimate of the $B_{1t}$ map to determine the white matter region, and apply a high-pass filter to the first estimate of the $B_{1t}$ map to determine the gray matter region. The processor 104 can also apply an erosion algorithm to each mask to avoid interference or overlap between regions associated with different tissue types. For each of the masks generated by the processor 104, pixels associated with the corresponding tissue type can have a value equal to 1 (or a non-zero value) whereas other pixels can have a value equal to zero.

Figure 5B:
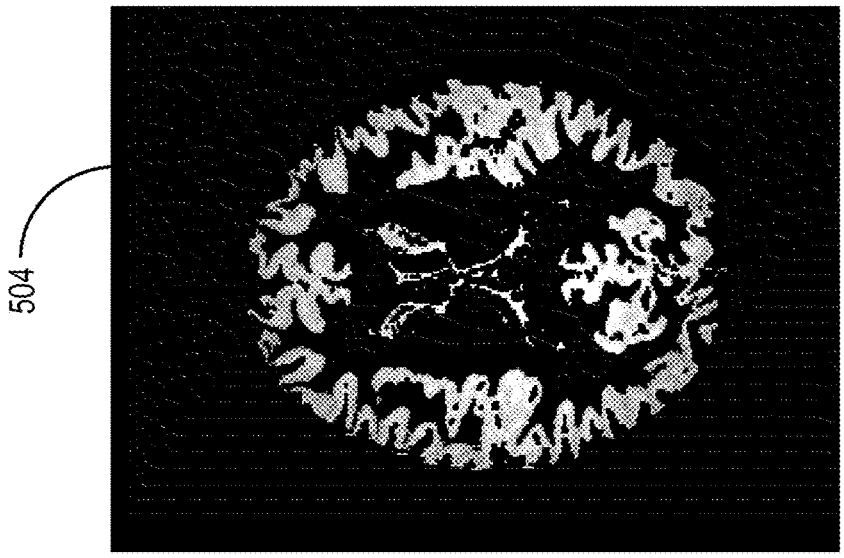
FIGS. 5A and 5B show images representing masks for white matter and gray matter.
Figure 5A:
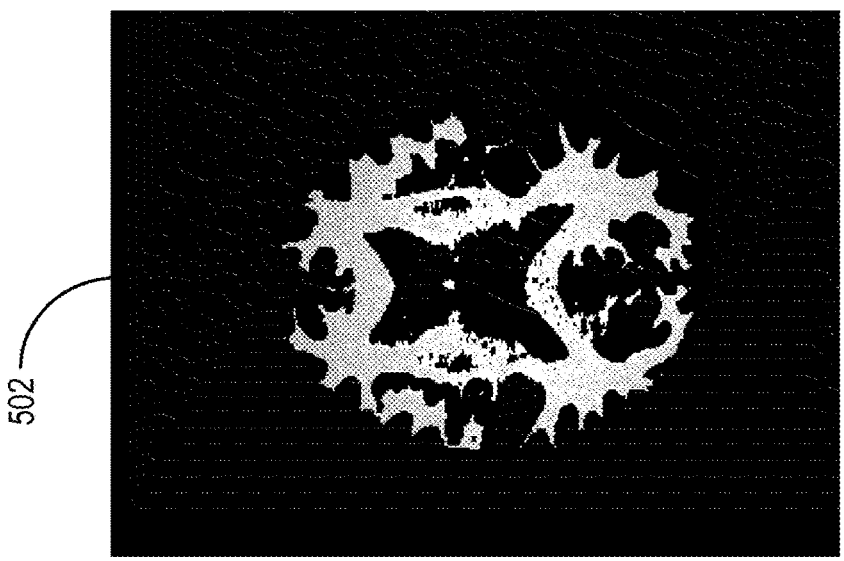

Referring to FIGS. 5A and 5B, images representing masks for white matter and gray matter are shown. The image 502 represents a mask of the white matter, and the image 504 represents a mask of the gray matter. Both masks are generated using the first estimate of the $B_{1t}$ map shown in FIG. 4B.

Figures 6A, 6B:
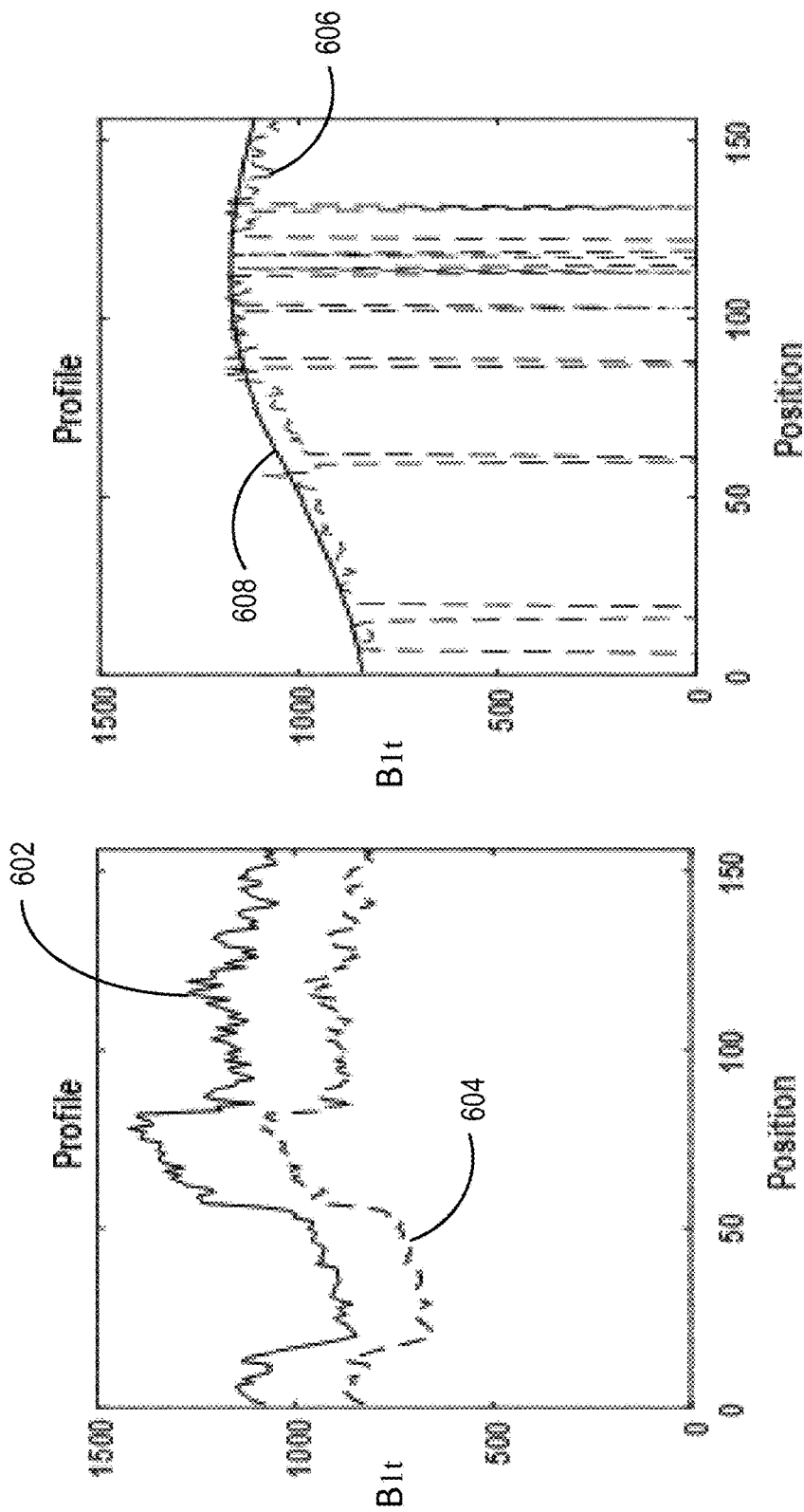
FIG. 6A shows plots of a first estimate of $B_{1t}$ and a second estimate of $B_{1t}$ across a line within the anatomical region.
FIG. 6B shows plots associated with a merged $B_{1t}$ map with and without local quadratic fitting.

At step 210, the processor 104 can generate a third $B_{1t}$ map using the estimated first $B_{1t}$ and the estimated second $B_{1t}$ map. Referring to FIG. 6A, plots of the first estimate of $B_{1t}$ and the second estimate of $B_{1t}$ across a line within the anatomical region are shown. The plot 602 represents the first estimate of $B_{1t}$ (or an estimate of $B_{1t}$ using a constant value of $T_1$ corresponding to white matter) across the line within the anatomical region. The plot 604 represents the second estimate of $B_{1t}$ (or an estimate of $B_{1t}$ using a constant value of $T_1$ corresponding to gray matter) across the line within the anatomical region. Comparing the two plots 602 and 604, one can see that the first estimate of $B_{1t}$ and the second estimate of $B_{1t}$ are substantially shifted versions of one another. Generating the third $B_{1t}$ map can include the processor 104 shifting at least one of the first and second estimated maps of $B_{1t}$ until both the first and second estimated maps of $B_{1t}$ substantially overlap. For example, the processor 104 can shift the first estimated map of $B_{1t}$ by a shift value such that the mean square error between the shifted first estimated map of $B_{1t}$ and the second estimated map of $B_{1t}$ is minimized.

The processor 104 can generate the third $B_{1t}$ map using the shifted first estimated map of $B_{1t}$, the second estimated map of $B_{1t}$, and the masks corresponding to the first and second tissue types. In particular, the processor can (i) multiply (i.e., pixel by pixel multiplication) the mask corresponding to the first tissue type (e.g., white matter) with the shifted first estimated map of $B_{1t}$, multiply (i.e., pixel by pixel multiplication) the mask corresponding to the second tissue type (e.g., gray matter) with the second estimated map of $B_{1t}$, and (iii) merge the results of these multiplications to form a merged map of $B_{1t}$ (or the third $B_{1t}$ map). The processor 104 may apply local quadratic fitting to the merged map of $B_{1t}$ (or the third $B_{1t}$ map) to fill in (or assign values to) any pixels that do not belong to any of the generated masks.

Referring to FIG. 6B, plots associated with the merged $B_{1t}$ map with and without local quadratic fitting are depicted. The plot 606 represents values of the merged $B_{1t}$ across a line within the anatomical region. The plot 608 represents the same values of the merged $B_{1t}$ across the line within the anatomical region after applying local quadratic fitting. Local quadratic fitting can be achieved using a local quadratic fitting matrix of size m×m, where m is an integer. is used to create a smooth less noisy result throughout the entire n×n image. As illustrated in FIG. 6B, the local quadratic fitting operation leads to a smooth and less noise map of $B_{1t}$.

Figure 7B:
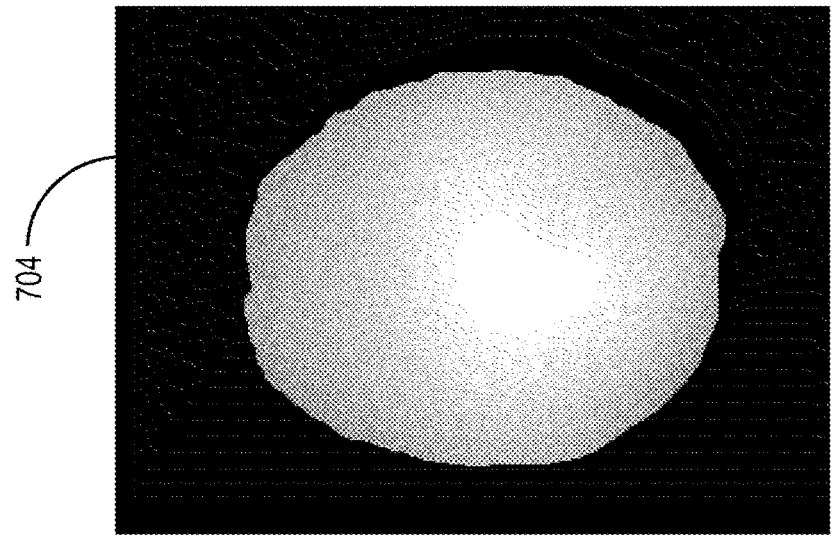
FIGS. 7A and 7B show images illustrating an example merged $B_{1t}$ map and example $B_{1t}$ map obtained after applying local quadratic fitting to the merged $B_{1t}$ map.
Figure 7A:
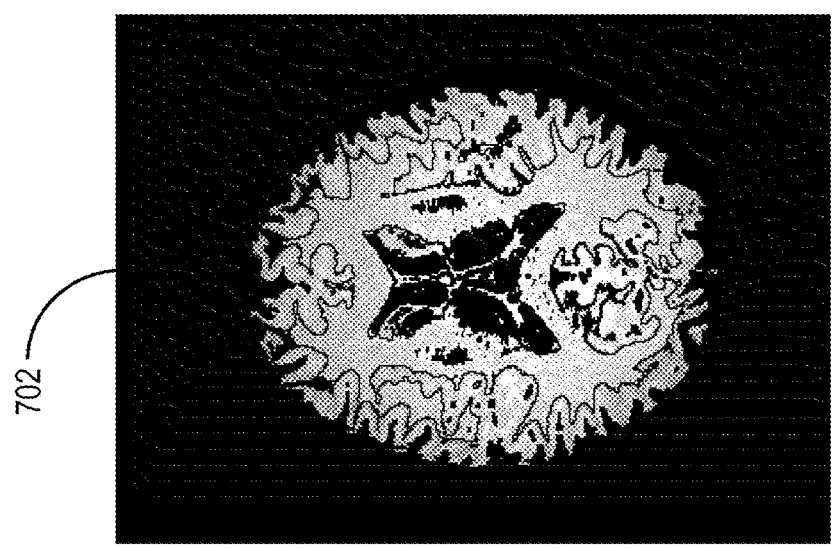

Referring to FIG. 7A, an image 702 illustrating an example merged $B_{1t}$ map is shown. In particular, the image 702 represents the resulting image when merging the multiplicative product of the mask 502 corresponding to the white matter and the shifted first estimated map of $B_{1t}$ and the multiplicative product of the mask 504 corresponding to the gray matter and the second estimated map of $B_{1t}$. The black regions in the image 702 represent pixels or regions that belong neither to mask 502 nor to mask 504.

Referring to FIG. 7B, an image 704 of $B_{1t}$ map obtained after applying local quadratic fitting to image 702 is shown. As illustrated in image 704, the local quadratic fitting allows for filling in the gaps in the merged $B_{1t}$ shown in FIG. 702. The $B_{1t}$ map shown in image 704 provides a reliable estimate of $B_{1t}$ within the anatomical region and allows for accurate reconstruction of the $T_1$ map and/or the SD map.

While the method 200 is described above with respect to two tissue types, the anatomical region can include more than two different tissue types. For instance, the anatomical region can include three distinct tissue types. In such instance, the processor 104 can further determine another estimate of the $B_{1t}$ map by scaling the $T_{1app}$ map (generated at step 204) by a third constant value of $T_1$ associated with the third tissue type within the anatomical region. The processor 104 can also generate a third mask representative of the region occupied by the third tissue type within the anatomical region. For example, the processor 104 can use different filters (e.g., low-pass filter(s), band-pass filter(s), and/or a high-pass filter(s)) to generate each of the three masks. The processor 104 can update the third $B_{1t}$ map using the map of $B_{1t}$ estimated based on the third constant value of $T_1$ (e.g., according to the third mask). Alternatively, the processor 104 can (initially) generate the third $B_{1t}$ map using the three estimates of the $B_{1t}$ map (e.g., based on the three masks corresponding to the three tissue types). For instance, the third tissue type can be cerebro-spinal fluid and the processor 104 can (i) multiply the first $B_{1t}$ map estimated based the constant $T_1$ value for white matter by the first mask, (ii) multiply the second $B_{1t}$ map estimated using the constant $T_1$ value for gray matter by the second mask, (iii) multiply the $B_{1t}$ map estimated using the constant $T_1$ value for cerebro-spinal fluid by the third mask, and (iv) so on for other tissues. The constant $T_1$ value for cerebro-spinal fluid can be equal to 4500 ms. The processor 104 can then merge the resulting images (from the multiplications with masks) to create a single more accurate $B_{1t}$ map image.

In some implementations, the processor 104 may remove local noise spikes by using, for example, a sliding window to calculate the mean and standard deviation in the window and remove those points (or pixels) that lie beyond a given threshold value (e.g., three standard deviations of the noise) above or below the mean. The processor 104 can apply local quadratic fitting as described above with regard to FIG. 6B to the merged $B_{1t}$ map using, for example, a local quadratic fitting matrix of size m×m to provide a smooth and less noisy $B_{1t}$ map image, where m is an integer. In some implementations, the integer m can be equal to 20. However, other values for m may be used. While in the case of the human brain the tissue types can include white matter, gray matter, and cerebro-spinal fluid, the methods and systems are to be interpreted as limited to the human brain or to these tissue types. In general, the methods described herein are not to be restricted to a specific anatomical region or to a specific number of tissue types within the anatomical region.

The method 200 can further include the processor 104 using the $B_{1t}$ map determined at step 210 to generate a first estimate of the $T_1$ map. The processor 104 can use equation (5) and divide the $T_{1app}$ map determined at step 204 by the square of the $B_{1t}$ map determined at step 201. Specifically, for each pixel or voxel x of the anatomical region, the processor 104 can compute the corresponding $T_1$ value as $$T_1(x) = \frac{T_{1app}(x)}{B_{1t}^2(x)}.$$

As such, this first estimate of the $T_1$ map accounts for the variation in the distribution of $B_{1t}$ within the anatomical region, and may be referred to as the corrected $T_1$ map.

The processor 104 can further generate an apparent spin density (SDapp) map using the first MR dataset and the second MR dataset. The $SD_{app}$ map represents the spatial distribution of $SD_{app}$ within the anatomical region. The processor 104 can determine the $SD_{app}$ map using equation (3) and the constant value of $B_{1t}$ assumed at step 204. For example, the processor 104 can solve equation (3) for $SD_{app}$ at each pixel using data points from the datasets corresponding to the FAs $\theta_1$ or $\theta_2$ and the constant value of $B_{1t}$ assumed at step 204. Alternatively, based on equation (2) and referring back to step 204, the processor 104 can determine $SD_{eff}\cdot(1-E1)$ at each pixel based on the intersection of the line defined by the data points $$\left(\frac{S(\theta_1)}{\tan(B_{1t}\theta_1)}, \frac{S(\theta_1)}{\sin(B_{1t}\theta_1)}\right)$$

and $$\left(\frac{S(\theta_2)}{\tan(B_{1t}\theta_2)}, \frac{S(\theta_2)}{\sin(B_{1t}\theta_2)}\right)$$

with the x-axis in the $$\left(\frac{S(\theta)}{\tan(B_{1t}\theta)}, \frac{S(\theta)}{\sin(B_{1t}\theta)}\right)$$

coordinate system when assuming a normalized constant value of $B_{1t}$ (e.g., $B_{1t}=1.0$). Since $E_1$ is already determined at step 204, the processor 104 can generate a map of $SD_{eff}$ by dividing the value corresponding to the intersection with the x-axis by $1-E_1$ at each pixel, and multiply the SDeff map by the constant value of $B_{1t}$ assumed at step 204 to generate the $SD_{app}$ map.

The processor 104 can generate a first estimate of the SD map by dividing the determined $SD_{app}$ map by the $B_{1t}$ map determined at step 210. According to Equation (4), for each pixel or voxel within the anatomical region, the processor 104 can scale (or divide) the $SD_{app}$ value at that pixel by the $B_{1t}$ value at the same pixel (from the $B_{1t}$ map generated at step 210). The generated first estimate of the SD map is an estimate of the $SD_{eff}$ map since $SD_{eff}=SD \cdot B_{1r} \cdot e^{-TE/T2^*}$. This first estimate of the SD map accounts for the variation in the distribution of $B_{1t}$ (but not the variation in the distribution of $B_{1r}$). Once the $B_{1r}$ data are obtained, a corrected SD map can be obtained via $SD_{cor}=SD \cdot e^{-TE/T2^*}$ and may be referred to as the corrected SD map. Finally, using multiple echoes to calculate T2*, the absolute SD can be obtained from the formula $SD=SD_{cor} \cdot e^{TE/T2^*}$.

Referring to FIGS. 8A-8C, images 802, 804 and 806 illustrate examples of an estimate of a $T_1$ map, an estimate of a $SD_{app}$ map, and an estimate of a SD map, respectively. The $T_1$ map shown in image 802 is generated by scaling (on a pixel by pixel basis) the $T_{1app}$ map in in image 402 (shown in FIG. 4A) by the square of $B_{1t}$ shown in image 704 (FIG. 7B). The estimate of the $SD_{app}$ map in image 804 is generated using Equation (3), one of the datasets illustrated in images 302 or 304 (FIGS. 3A and 3B). The estimate of the SD map (or $SD_{eff}$ map) of image 806 is generated by dividing the $SD_{app}$ map of image 704 by the $B_{1t}$ map of image 704 (FIG. 7B).

The processor 104 can use the estimated $B_{1t}$ map (determined at step 210), the corrected $T_1$ map and the corrected SD map to estimate (or generate) a map of $B_{1r}$. In particular, the processor 104 can employ the estimated $B_{1t}$ map as well as the corrected $T_1$ and SD maps to synthesize a MR dataset corresponding to a specific flip angle that can make a first region associated with a first tissue type (e.g., white matter) and a second region associated with a second tissue type (e.g., gray matter) isointense. The processor 104 can synthesize such a MR dataset without additional MR data acquisition via the MRI scanner 102, but rather by using Equation (1). The processor 104 may further vary the echo time TE to create a MR dataset where three regions corresponding to three different tissue types (e.g., white matter, gray matter, and cerebro-spinal fluid) are isointense. The processor 104 can scale the SD map estimate (e.g., the SD map shown in image 806 of FIG. 8C) by the estimated $B_{1r}$ map to alleviate the effect of the spatial variation of $B_{1r}$ within the anatomical region and achieve an improved estimate of the SD map.

Figure 9:
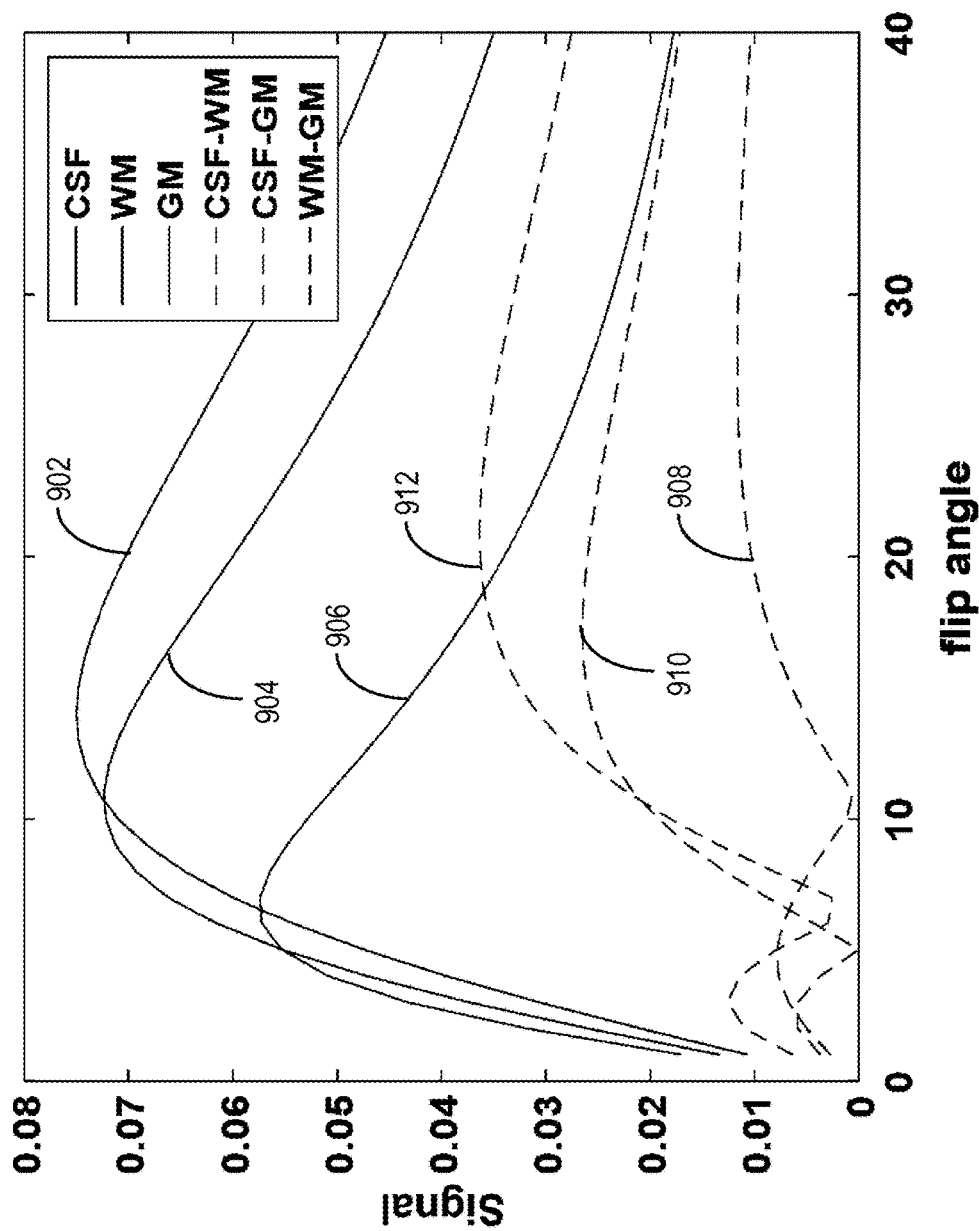
FIG. 9 shows example signals corresponding to different tissue types over a range of FAs.

Referring to FIG. 9, example signals corresponding to different tissue types over a range of FAs are shown. The signal 902 corresponds to white matter (or WM), signal 904 corresponds to gray matter (or GM), and signal 906 corresponds to cerebro-spinal fluid (or CSF). The signal 908 represents the difference between signals 902 and 904, the signal 910 represents the difference between signals 904 and 906, and the signal 912 represents the difference between signals 902 and 906. The signals 902, 904, and 906 were generated using constant $T_1$ values equal to 1000 ms within white matter, 1700 ms within gray matter, and 4500 ms within cerebro-spinal fluid. The repetition time TR is equal to 30 ms, the white matter SD is equal to 0.68 and the SD of gray matter is equal to 0.82. Also, the $T_2^*$ values of 44 ms and 51 ms were used for white matter and gray matter, respectively. signals 902 and 904 intersect at a FA about (or slightly above) 10°. By making different tissues isointense, the processor 104 can avoid the need to determine the local spin density. Since all signals are isointense, the amplitude variation in the synthesized dataset represents the variation in the $B_{1r}$ field. Accordingly, the processor 104 can determine (or generate) a $B_{1r}$ map based on the synthesized data set. The processor 104 may also employ local quadratic fitting in estimating the $B_{1r}$ map. The $B_{1r}$ map used to correct the initial images can be defined as the signal from the isointense image normalized to the value of $B_{1r}$ in the center of the image.

Figure 10:
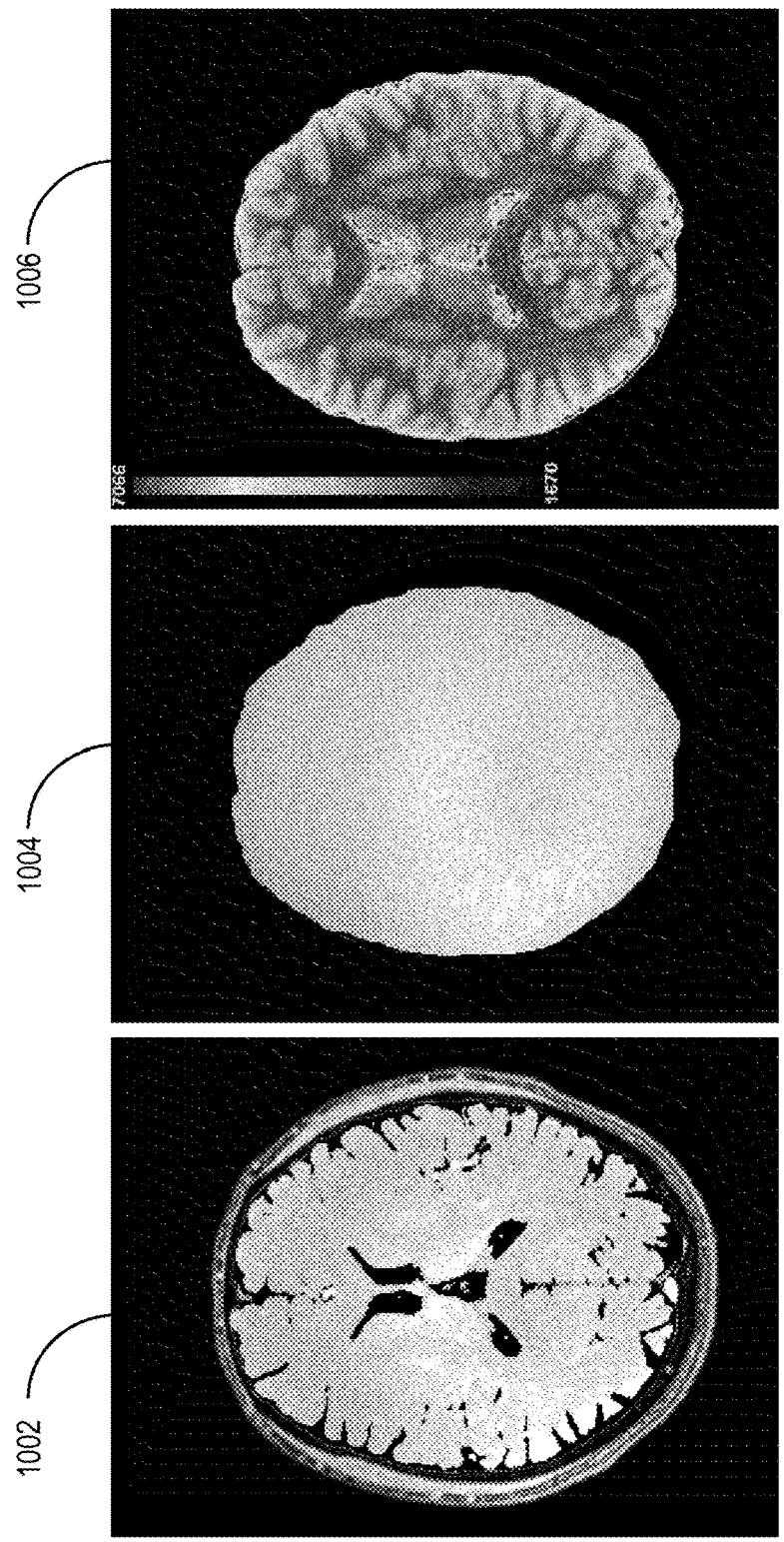
FIGS. 10A-10C show images illustrating an example synthesized MR dataset, an example receive RF field, and an example scaled spin density map, respectively.

Referring to FIGS. 10A-10C, images illustrating an example synthesized MR dataset, an example receive RF field, and an example scaled spin density map are shown. Image 1002 represents a double isointense MR dataset where the FA is selected such that the white matter and the gray matter are isointense. The image 1004 represents a $B_{1r}$ map generated (or estimated) based on the isointense MR dataset of image 1002. The isointense MR dataset in image 1002 includes gaps (black regions or pixels). Such gaps are eliminated in the $B_{1r}$ map of image 1004 by using local quadratic fitting. In some implementations, the processor 104 may scale the SD map estimate (e.g., the SD map shown in image 806 of FIG. 8C) by the $B_{1r}$ map estimated based on the synthesized dataset to alleviate the effect of the spatial variation of $B_{1r}$ within the anatomical region on the estimated SD map. The image 1006 represents a scaling (pixel-by-pixel scaling) of the SD map in image 806 by the $B_{1r}$ map of image 1004. Comparing the images 1006 and 806, one can see that the SD map in image 1006 provides an improved representation of the various sub-regions within the anatomical region compared to image 806.

In some implementations, the processor 104 (or some other computing device) can estimate a plurality of $B_{1t}$ maps for a plurality of subjects (e.g., patients or volunteers). The processor 104 may estimate the $B_{1t}$ map for each subject as described above with regard to method 200. For each subject, the processor 104 can transform the corresponding $B_{1t}$ map for each subject into a respective template of the anatomical region (e.g., brain). The processor 104 can accomplish this by first transforming the magnitude image of the first dataset into a template brain (e.g., using Insight Segmentation, and Registration Toolkit (ITK)). The processor 104 can use the resulting transformation to map the $B_{1t}$ field into the template space. The processor 104 can then average the $B_{1t}$ values in the templates associated with the plurality of subjects into a common $B_{1t}$ template. In some implementations, the averaging can be a weighted averaging. For example, some templates associated with some subjects may be weighted more or less than other templates. The processor 104 can use the common (or average) $B_{1t}$ template as an estimate of the $B_{1t}$ map for various patients by performing an inverse transform back to the patient space. For instance, the common (or average) $B_{1t}$ template can be computed offline and used in reconstructing $T_1$ maps or SD maps (as described above with regard to the $B_{1t}$ map generated at step 201) for various patients. By using the common (or average) $B_{1t}$ template, the processor 104 may avoid generating a $B_{1t}$ map for each new scanned subject and instead use the pre-computed common (or average) $B_{1t}$ template. In some implementations, the processor can use both the precomputed common (or average) $B_{1t}$ template and an estimate of the $B_{1t}$ map specific to the patient to generate separate images of the anatomical region (e.g., separate images of the $T_1$ map).

The processor 104 (or some other computing device) can also generate a common (or average) $B_{1r}$ template. The processor 104 can estimate a plurality of $B_{1r}$ maps for a plurality of subjects (e.g., patients or volunteers), for example, based on synthesized MR datasets with isointense regions for separate subjects as described above. For each subject, the processor 104 can transform the corresponding $B_{1r}$ map into a respective template of the anatomical region (e.g., brain), and average (e.g., weighted or non-weighted averaging) the templates for various subjects to generate a common (or average) $B_{1r}$ template. The common (or average) $B_{1r}$ template can be computed offline, and the processor 104 can use the common (or average) $B_{1r}$ template as an estimate of the $B_{1r}$ map for various patients. The availability of a precomputed common (or average) $B_{1r}$ template can allow avoiding the construction (or computation) of a respective $B_{1r}$ map for each newly scanned patient. In some implementations, the processor can use both the precomputed common (or average) $B_{1r}$ template and an estimate of the $B_{1r}$ map specific to the patient to generate separate images of the anatomical region.

Figure 11:
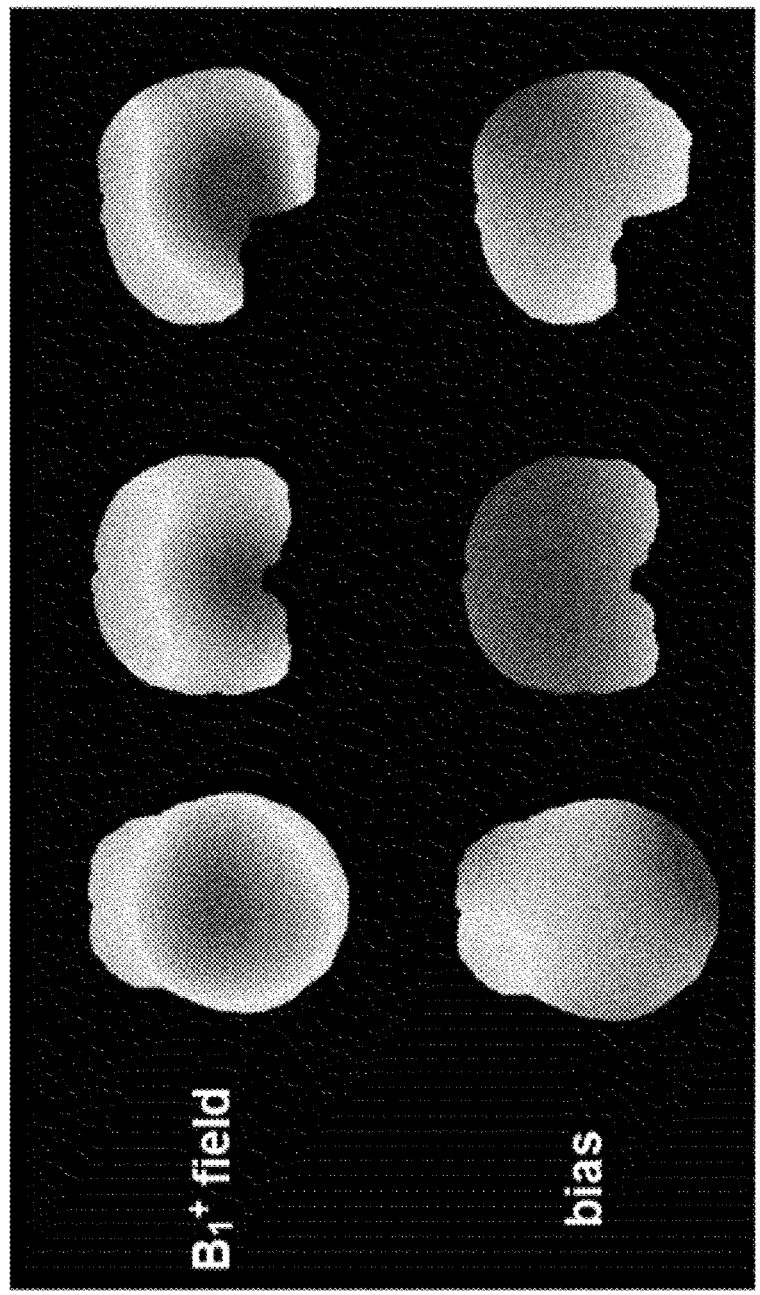
FIG. 11 shows examples of brain templates for the $B_{1t}$ and $B_{1r}$ maps.
Figure 12B:
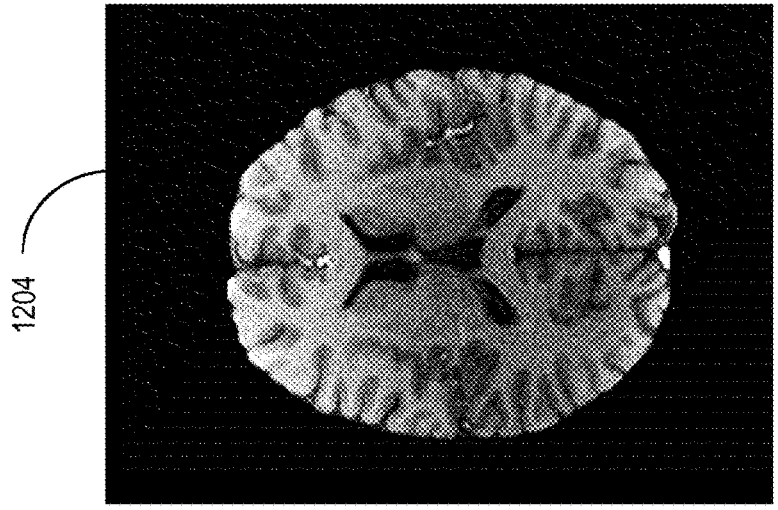
FIGS. 12A-12D show images illustrating scaled MR datasets and subtraction MR images.
Figure 12A:
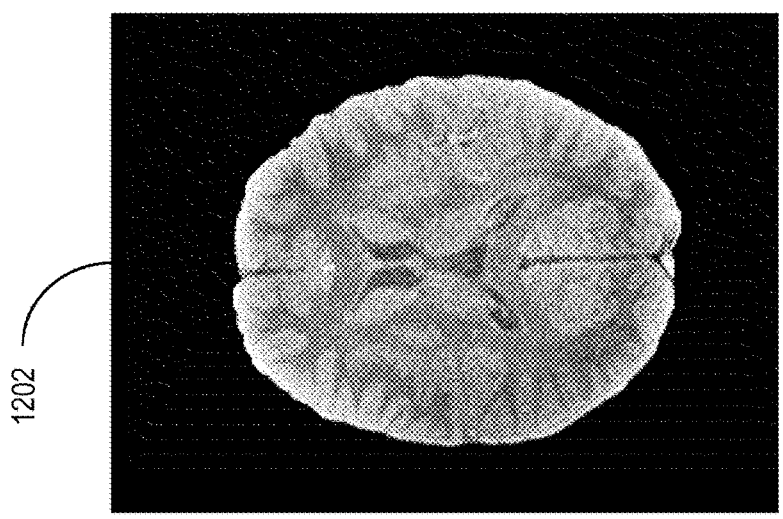
Figure 12D:
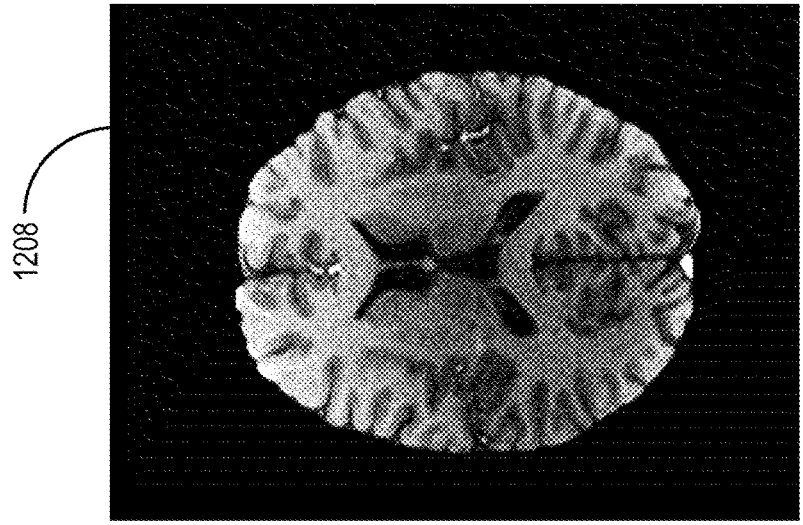
Figure 12C:
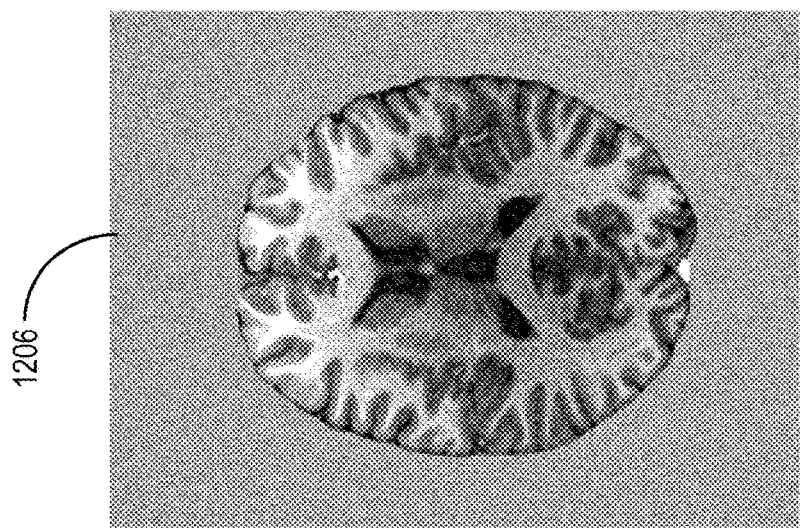

Referring to FIG. 11, examples of brain templates for the $B_{1t}$ and $B_{1r}$ map are shown. The upper row of images illustrates an example common (or average) brain template for the $B_{1t}$ map. This common (or average) template represents an estimate of the $B_{1t}$ map that can be used for various subjects. The lower row of images illustrates an example common (or average) brain template for the $B_{1r}$ map. This common (or average) template represents an estimate of the $B_{1r}$ map that can be used for various subjects.

For each scanned subject, the processor 104 can inverse transform the average $B_{1t}$ template (e.g., using ITK) and/or the average $B_{1r}$ template for that specific subject. For instance, the processor can adjust the common (or average) $B_{1t}$ template and/or the common (or average) $B_{1r}$ template to conform with the size of the anatomical region (e.g., brain) for a specific patient. The processor 104 may use the inverse transformed common (or average) $B_{1t}$ template to estimate the $T_1$ map for that specific patient. In particular, the processor 104 can scale (or divide on a pixel-by-pixel or voxel-by-voxel basis) the $T_{1app}$ map for the patient by the square of the inverse transformed common (or average) $B_{1t}$ template to generate an estimate of the $T_1$ map. Such estimate can either substitute the estimate based on an estimated $B_{1t}$ map specific to the patient or can be an additional (or second) estimate of the $T_1$ map. The processor 104 may also use the common (or average) $B_{1t}$ when estimating the SD (or $SD_{eff}$) map for the patient. In particular, the processor 104 may scale (or divide on a pixel-by-pixel or voxel-by-voxel basis) the $SD_{app}$ map for the patient by the inverse transformed common (or average) $B_{1t}$ template to generate an estimate of the SD map.

The processor 104 can also scale the original datasets (corresponding to FAs $\theta_1$ and $\theta_2$) acquired at step 202 by the $B_{1r}$ map estimated based on the synthesized dataset, and generate a MR image of the anatomical region by subtracting the scaled datasets. The generated MR image can illustrate the various tissue types within the anatomical regions based on the respective $T_1$ values. The processor 104 can employ a weighted subtraction when subtracting a first scaled MR dataset corresponding to the first FA from the other scaled dataset corresponding to the second FA. In some implementations, the processor 104 can scale the original datasets (corresponding to FAs $\theta_1$ and $\theta_2$) acquired at step 202 by the common (or average) $B_{1r}$ template computed or reconstructed offline (or an inverse transformation thereof). In some implementations, the processor 104 may scale the SD map estimate (e.g., the SD map shown in image 806 of FIG. 8C) by the common (or average) $B_{1r}$ template to alleviate the effect of the spatial variation of $B_{1r}$ within the anatomical region on the estimated SD map.

In some implementations, the processor 104 can subtract (without scaling) images corresponding to the original datasets (corresponding to FAs $\theta_1$ and $\theta_2$) acquired at step 202 to generate another (or an alternative) MR image of the anatomical region. Such MR images can illustrate the various tissue types within the anatomical regions based on the respective $T_1$ values.

Referring to FIGS. 12A-12D, images of scaled MR datasets and subtraction MR images are illustrated. Images 1202 and 1204 represent scalings of images 302 and 304, respectively, by the $B_{1r}$ map in image 1002. The images 1202 and 1204 represent an improvement over the corresponding original images 302 and 304 since the scaling by the $B_{1r}$ map alleviates the effect of the spatial variation of $B_{1r}$ within the anatomical region. However, images 1202 and 1204 still suffer from the effect of the spatial variation of $B_{1t}$ within the anatomical region. The image 1206 represents a subtraction between the images 302 and 304 (e.g., subtracting the image corresponding to the low FA from the image corresponding to the large FA) corresponding to the original acquired datasets for the two FAs. The image 1208 represents a subtraction between the scaled images 1202 and 1204 (e.g., subtracting the image corresponding to the low FA from the image corresponding to the large FA). While both images 1206 and 1208 provide an improved representation of the various tissues within the anatomical region compared to the images 302 and 304 corresponding to the original acquired data, the image 1208 represents an improvement over image 1206 since the effect of the spatial variation of $B_{1r}$ within the anatomical region is eliminated (or alleviated) in the former image 1208.

The methods and system described herein provide various techniques for generating improved images of anatomical regions scanned using two flip angles. These methods and system are not to be interpreted as limited to human brain and can be used for other anatomical regions. Also, while this disclosure describes various techniques described for generating various MR images (e.g., of the estimated $T_1$ map, the estimated SD map, the scaled SD map, the subtraction MR image, the scaled subtraction MR image, the estimated $B_{1t}$ map, the estimated $B_{1r}$ map, the common $B_{1t}$ template, or the common $B_{1r}$ template), this disclosure should be interpreted as encompassing various combinations of such techniques or corresponding MR images. Furthermore, the process 104 can apply the techniques for generating various MR images described herein for multiple echo times. For instance, the processor 104 can apply averaging or weighted averaging to MR images (e.g., $B_{1t}$ maps, $B_{1r}$ maps, $T_{1app}$ maps, $T_1$ maps, $SD_{app}$ maps, SD maps, etc.) generated based on datasets associated with the various echo times to provide improved images of anatomical regions.

A person skilled in the art should appreciate that processes described in this disclosure can be implemented using computer code instructions executable by a processor. The computer code instructions can be stored on a non-transitory or tangible computer-readable medium such as a random access memory (RAM), a read only memory (ROM), a cache memory, a disc memory, any other memory, or any other computer readable medium. Processes described in this disclosure can be implemented by an apparatus including at least one processor and/or memory storing executable code instructions. The code instructions when executed by the at least one processor can cause performing at least one of the processes or operations described in this disclosure. The apparatus can for example be a MRI scanner, a computer device or other electronic device associated with a MRI scanner.

What is claimed is:

1. A magnetic resonance imaging (MRI) system comprising:
   a MRI scanner configured to acquire a first magnetic resonance (MR) dataset corresponding to a first flip angle and a second MR dataset corresponding to a second flip angle by imaging an anatomical region using at least one echo time;
   at least one processor; and
   a memory, with computer code instructions stored thereon, the computer code instructions, when executed by the at least one processor, cause the at least one processor to:
      generate an apparent longitudinal relaxation time ($T_{1app}$) map, representing a spatial distribution of T1app within the anatomical region using the first MR dataset, the second MR dataset and a constant value for a transmit radio frequency (RF) field within the anatomical region;
      estimate a first transmit RF field map by scaling the $T_{1app}$ map by a first constant value of longitudinal relaxation time ($T_1$), the first constant value of $T_1$ associated with a first tissue type within the anatomical region;
      estimate a second transmit RF field map by scaling the $T_{1app}$ map by a second constant value of $T_1$, the second constant value of $T_1$ associated with a second tissue type within the anatomical region; and
      generate a third transmit RF field map using the estimated first transmit RF field map and the estimated second transmit RF field map, the third transmit RF field map representing a spatial distribution of the transmit RF field within the anatomical region.

2. The MRI system of claim 1, wherein the anatomical region is a human brain, the first tissue type is white matter, and the second tissue type is gray matter.

3. The MRI system of claim 1, wherein the computer code instructions, when executed by the at least one processor, further cause the at least one processor to:
   estimate a fourth transmit RF field map by scaling the $T_{1app}$ map by a third constant value of $T_1$, the third constant value of $T_1$ associated with a third tissue type within the anatomical region,
   wherein generating the third transmit RF field map includes using the estimated first transmit RF field map, the estimated second transmit RF field map, and the estimated fourth transmit RF field map.

4. The MRI system of claim 3, wherein the anatomical region is a human brain, the first tissue type is white matter, the second tissue type is gray matter and the third tissue type is cerebro-spinal fluid.

5. The MRI system of claim 1, wherein the computer code instructions, when executed by the at least one processor, further cause the at least one processor to:
   generate a first longitudinal relaxation time ($T_1$) map by dividing the $T_{1app}$ map by the square of the third transmit RF field map, the first $T_1$ map representing the spatial distribution of $T_1$ within the anatomical region.

6. The MRI system of claim 1, wherein the computer code instructions, when executed by the at least one processor, further cause the at least one processor to:
   generate an apparent spin density ($SD_{app}$) map using the first MR dataset, the second MR dataset, and the constant value for the transmit RF field, the $SD_{app}$ map representing a spatial distribution of $SD_{app}$ within the anatomical region;
   generate a first spin density (SD) map by scaling the $SD_{app}$ map by the third transmit RF field map;
   synthesize, using the third transmit RF field map, the first $T_1$ map, and the first SD map, a third MR dataset corresponding to a third flip angle such that at least a first sub-region of the anatomical region corresponding to the first tissue type and a second sub-region of the anatomical region corresponding to the second tissue type are isointense;
   estimate a receive RF field map using the synthesized third MR dataset, the receive RF field map representing spatial distribution of a receive RF field within the anatomical region; and
   generate a second SD map by scaling the first SD map by the estimated receive RF field map.

7. The MRI system of claims 1, wherein the computer code instructions, when executed by the at least one processor, cause the at least one processor to:
   estimate a plurality of transmit RF field maps for a plurality of subjects; and
   generate a transmit RF field template using an averaging of the estimated plurality of transmit RF field maps for the plurality of subjects.

8. The MRI system of claim 7, wherein the computer code instructions, when executed by the at least one processor, cause the at least one processor to generate a second $T_1$ map using the $T_{1app}$ map and the transmit RF field template.

9. The MRI system of claim 7, wherein the computer code instructions, when executed by the at least one processor, cause the at least one processor to generate a spin density (SD) map using an estimated $SD_{app}$ map, the transmit RF field template, and an estimated receive RF field map.

10. The MRI system of claim 6, wherein the computer code instructions, when executed by the at least one processor, cause the at least one processor to:
    scale the first MR dataset by the receive RF field map;
    scale the second MR dataset by the receive RF field map; and
    generate an image representing a weighted subtraction of the scaled first MR dataset from the scaled second MR dataset.

11. The MRI system of claim 1, wherein the computer code instructions, when executed by the at least one processor, cause the at least one processor to generate an image representing a weighted subtraction of the first MR dataset from the second MR dataset.

12. A method for magnetic resonance imaging (MRI), comprising:
    receiving, by at least one processor, a first magnetic resonance (MR) dataset corresponding to a first flip angle and a second MR dataset corresponding to a second flip angle, the first MR dataset and the second MR dataset acquired by imaging an anatomical region using at least one echo time;
    generating, by at least one processor, an apparent longitudinal relaxation time ($T_{1app}$) map, representing a spatial distribution of $T_{1app}$ within the anatomical region using the first MR dataset, the second MR dataset and a constant value for a transmit radio frequency (RF) field within the anatomical region;
    estimating, by the at least one processor, a first transmit RF field map by scaling the $T_{1app}$ map by a first constant value of longitudinal relaxation time ($T_1$), the first constant value of $T_1$ associated with a first tissue type within the anatomical region;
    estimating, by the at least one processor, a second transmit RF field map by scaling the $T_{1app}$ map by a second constant value of $T_1$, the second constant value of $T_1$ associated with a second tissue type within the anatomical region; and generating, by the at least one processor, a third transmit RF field map using the estimated first transmit RF field map and the estimated second transmit RF field map, the third transmit RF field map representing a spatial distribution of the transmit RF field within the anatomical region.

13. The method of claim 12 further comprising:

estimating, by the at least one processor, a fourth transmit RF field map by scaling the $T_{1app}$ map by a third constant value of $T_1$, the third constant value of $T_1$ associated with a third tissue type within the anatomical region, wherein generating the third transmit RF field map includes using the estimated first transmit RF field map, the estimated second transmit RF field map, and the estimated fourth transmit RF field map.

14. The method of claim 12 further comprising:

generating, by the at least one processor, a first longitudinal relaxation time ($T_1$) map by dividing the $T_{1app}$ map by the square of the third transmit RF field map, the first $T_1$ map representing spatial distribution of $T_1$ within the anatomical region.

15. The method of claim 14 further comprising:

generating, by the at least one processor, an apparent spin density ($SD_{app}$) map using the first MR dataset, the second MR dataset, and the constant value for the transmit RF field, the $SD_{app}$ map representing spatial distribution of $SD_{app}$ within the anatomical region; and generating, by the at least one processor, a first spin density (SD) map by scaling the SDapp map by the third transmit RF field map;

synthesizing, by the at least one processor, using the third RF field map, the first $T_1$ map, and the first SD map, a third MR dataset corresponding to a third flip angle such that at least a first sub-region of the anatomical region corresponding to the first tissue type and a second sub-region of the anatomical region corresponding to the second tissue type are isointense;

estimating, by the at least one processor, a receive RF field map using the synthesized third MR dataset, the receive RF field map representing spatial distribution of a receive RF field within the anatomical region; and generating, by the at least one processor, a second SD map by scaling the first SD map by the estimated receive RF field map.

16. The method of claim 12 further comprising:

estimating, by the at least one processor, a plurality of transmit RF field maps for a plurality of subjects; and generating, by the at least one processor, a transmit RF field template using an averaging of the estimated plurality of transmit RF field maps for the plurality of subjects.

17. The method of claim 16 further comprising:

generating, by the at least one processor, a spin density (SD) map using an estimated $SD_{app}$ map, the transmit RF field template, and an estimated receive RF field map.

18. The method of claim 16 further comprising:

generating, by the at least one processor, a second $T_1$ map using the $T_{1app}$ map and the transmit RF field template.

19. The method of claim 15 further comprising:

scaling, by the at least one processor, the first MR dataset by the receive RF field map;

scaling, by the at least one processor, the second MR dataset by the receive RF field map; and generating, by the at least one processor, an image representing a weighted subtraction of the scaled first MR dataset from the scaled second MR dataset.

20. A non-transitory computer-readable medium comprising computer code instructions stored thereon, the computer code instructions when executed by a at least one processor cause the at least one processor to:

receive a first magnetic resonance (MR) dataset corresponding to a first flip angle and a second MR dataset corresponding to a second flip angle, the first MR dataset and the second MR dataset acquired by imaging an anatomical region using at least one echo time;

generate an apparent longitudinal relaxation time ($T_{1app}$) map, representing a spatial distribution of $T_{1app}$ within the anatomical region using the first MR dataset, the second MR dataset and a constant value for a transmit radio frequency (RF) field within the anatomical region;

estimate a first transmit RF field map by scaling the $T_{1app}$ map by a first constant value of longitudinal relaxation time ($T_1$), the first constant value of $T_1$ associated with a first tissue type within the anatomical region;

estimate a second transmit RF field map by scaling the $T_{1app}$ map by a second constant value of $T_1$, the second constant value of $T_1$ associated with a second tissue type within the anatomical region; and generate a third transmit RF field map using the estimated first transmit RF field map and the estimated second transmit RF field map, the third transmit RF field map representing a spatial distribution of the transmit RF field within the anatomical region.

* * * * *